US012569684B2

(12) United States Patent
Weerakoon et al.

(10) Patent No.: US 12,569,684 B2
(45) Date of Patent: Mar. 10, 2026

(54) CALIBRATION OF STIMULATION CIRCUITRY IN AN IMPLANTABLE STIMULATOR DEVICE USING SENSED NEURAL RESPONSES TO STIMULATION

(71) Applicant: Boston Scientific Neuromodulation Corporation, Valencia, CA (US)

(72) Inventors: Pujitha Weerakoon, Valencia, CA (US); Kiran K. Gururaj, Valencia, CA (US); Goran N. Marnfeldt, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 559 days.

(21) Appl. No.: 17/932,764

(22) Filed: Sep. 16, 2022

(65) Prior Publication Data

US 2023/0102847 A1    Mar. 30, 2023

Related U.S. Application Data

(60) Provisional application No. 63/261,586, filed on Sep. 24, 2021.

(51) Int. Cl.
*A61N 1/36* (2006.01)

(52) U.S. Cl.
CPC ....... *A61N 1/3615* (2013.01); *A61N 1/36062* (2017.08); *A61N 1/36139* (2013.01)

(58) Field of Classification Search
CPC .............. A61N 1/3615; A61N 1/36062; A61N 1/36139; A61N 1/0534; A61N 1/36125;
(Continued)

(56) References Cited

U.S. PATENT DOCUMENTS 6,516,227 B1   2/2003   Meadows et al.
8,606,362 B2   12/2013   He et al.
(Continued)

FOREIGN PATENT DOCUMENTS

WO   2021/003290 A1   1/2021
WO   2021/119741 A1   6/2021

OTHER PUBLICATIONS

International Search Report and Written Opinion regarding corresponding PCT Application No. PCT/US2022/076526, mailed Dec. 8, 2022.

(Continued)

*Primary Examiner* — George R Evanisko
(74) *Attorney, Agent, or Firm* — Lewis & Reese, PLLC

(57) ABSTRACT

Methods and circuitry for calibrating stimulation circuitry in an implantable stimulator device (ISD) is disclosed. The ISD can sense neural response to the stimulation, and use an algorithm to assess those responses and determine a therapeutic window for a particular stimulation parameter, such as amplitude. Stimulation circuitry in the ISD is programmed with information indicative of the determined therapeutic window, such as by programming a minimum and/or maximum current amplitude. As well as restricting operation of the stimulation circuitry to within the therapeutic amplitude window, such programming calibrates the stimulation circuitry and allows an expanded range of, or all of, amplitude values supported by the stimulation circuitry to be used, which allows the amplitude to be incremented in smaller current increments.

19 Claims, 12 Drawing Sheets

(58) Field of Classification Search
CPC ........... A61N 1/37235; A61N 1/36157; A61N
1/36135; A61N 1/36039
USPC .......................................................... 607/59
See application file for complete search history.

(56) References Cited

U.S. PATENT DOCUMENTS

| | | | |
|---|---|---|---|
| 8,620,436 | B2 | 12/2013 | Parramon et al. |
| 9,259,574 | B2 | 2/2016 | Aghassian et al. |
| 9,724,508 | B2 | 8/2017 | Lamont et al. |
| 9,925,379 | B2* | 3/2018 | Min .................. A61N 1/37241 |
| 10,525,253 | B2 | 1/2020 | Marnfeldt et al. |
| 10,716,937 | B2 | 7/2020 | Feldman et al. |
| 10,792,491 | B2 | 10/2020 | Feldman et al. |
| 10,842,996 | B2 | 11/2020 | Baru et al. |
| 10,881,859 | B2 | 1/2021 | Brill et al. |
| 10,912,942 | B2 | 2/2021 | Weerakoon et al. |
| 11,040,192 | B2 | 6/2021 | Weerakoon et al. |
| 2015/0080982 | A1 | 3/2015 | Funderburk |
| 2015/0231402 | A1 | 8/2015 | Aghassian |
| 2015/0360038 | A1 | 12/2015 | Zottola et al. |
| 2017/0296823 | A1 | 10/2017 | Hershey et al. |
| 2019/0275331 | A1 | 9/2019 | Zhu |
| 2019/0299006 | A1 | 10/2019 | Marnfeldt |
| 2020/0305744 | A1 | 10/2020 | Weerakoon et al. |
| 2020/0305745 | A1 | 10/2020 | Wagenbach et al. |
| 2020/0368542 | A1* | 11/2020 | Peterson ............ A61N 1/36071 |
| 2021/0252289 | A1* | 8/2021 | Esteller .................. A61B 5/388 |
| 2021/0275798 | A1 | 9/2021 | Marnfeldt |
| 2022/0040486 | A1 | 2/2022 | Moffitt |
| 2022/0241589 | A1* | 8/2022 | Crosby .............. A61N 1/36021 |

OTHER PUBLICATIONS

U.S. Appl. No. 17/654,343, Esteller et al., filed Mar. 10, 2022.
U.S. Appl. No. 17/654,345, Weerakoon et al., filed Mar. 10, 2022.

* cited by examiner

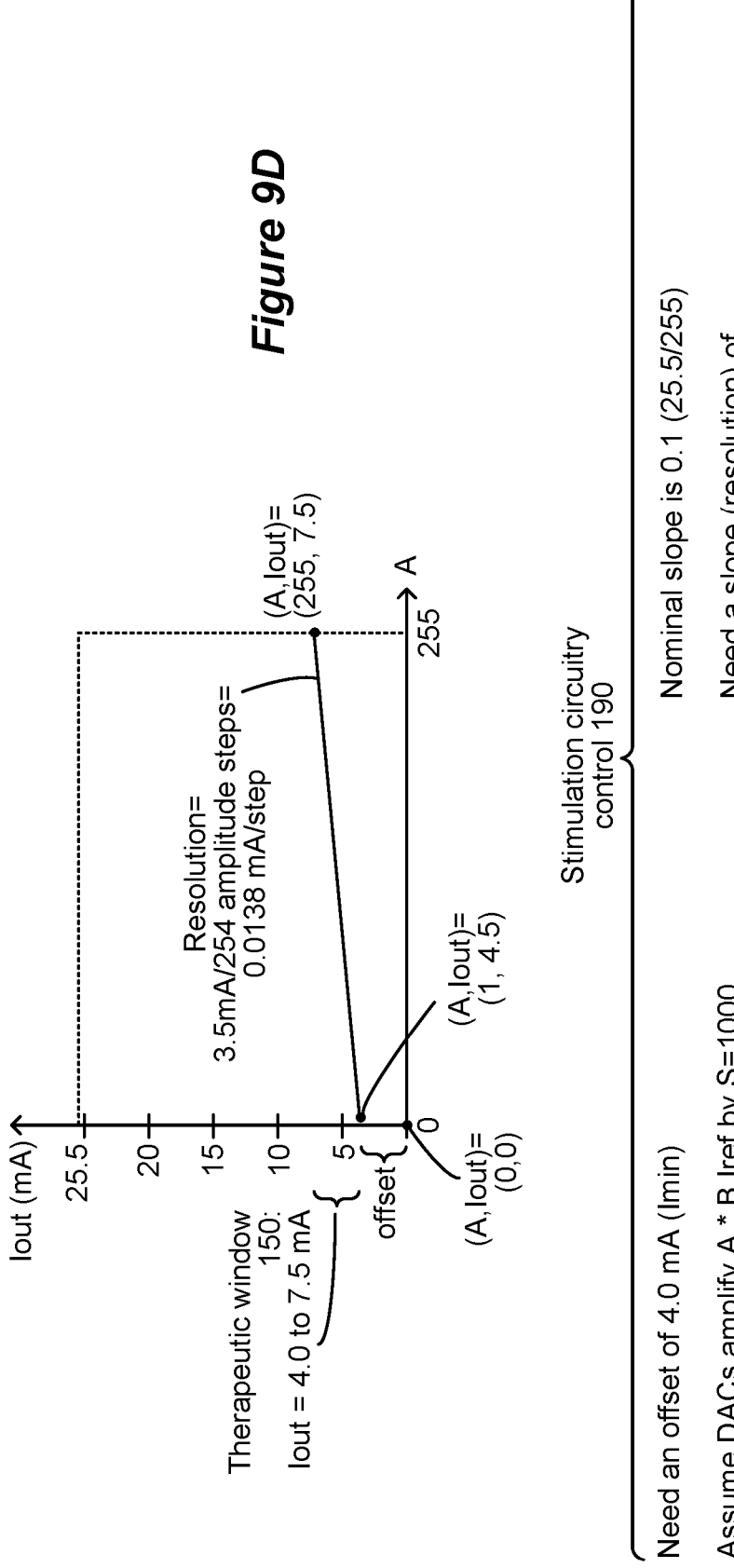

*Figure 9D*

Stimulation circuitry
control 190

Nominal slope is 0.1 (25.5/255)

Need a slope (resolution) of
(Imax-Imin/255-1) =
(7.5-4.0/255-1) = 0.0138 mA/step A*Iref needs a global gain B = 0.138 (0.0138/0.1)

This can be provided by the global gain DAC 202. The
closest gain value to 0.138 is 0.1375 (decimal 11, which
is produced by global gain control signals:
  B_10 to B_0 = asserted
  B_159 to B_11 = not asserted Need an offset of 4.0 mA (Imin)

Assume DACs amplify A * B Iref by S=1000.

The current at node 212 needs an global offset of
Δ = 4.0 μA

This can be provided by global offset DAC 206. The closest
value is 4 μA (decimal 4), which is produced by global offset
control signals:
  Δ_4 = not asserted
  Δ_3 = not asserted
  Δ_2 = asserted
  Δ_1 = not asserted
  Δ_0 = not asserted

CALIBRATION OF STIMULATION CIRCUITRY IN AN IMPLANTABLE STIMULATOR DEVICE USING SENSED NEURAL RESPONSES TO STIMULATION

CROSS REFERENCE TO RELATED APPLICATIONS

This is a non-provisional of U.S. Provisional Patent Application Ser. No. 63/261,586, filed Sep. 24, 2021, to which priority is claimed, and which is incorporated herein by reference.

FIELD OF THE INVENTION

This application relates to Implantable Medical Devices (IMDs), and more specifically to circuitry to assist with calibrating stimulation in an implantable stimulator device.

INTRODUCTION

Implantable neurostimulator devices are devices that generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder subluxation, etc. The description that follows will generally focus on the use of the invention within a Spinal Cord Stimulation (SCS) system, such as that disclosed in U.S. Pat. No. 6,516,227. However, the present invention may find applicability with any implantable neurostimulator device system, such as a Deep Brain Stimulator (DBS) system.

An SCS system typically includes an Implantable Pulse Generator (IPG) 10 shown in FIG. 1. The IPG 10 includes a biocompatible device case 12 that holds the circuitry and a battery 14 for providing power for the IPG to function. The IPG 10 is coupled to tissue-stimulating electrodes 16 via one or more electrode leads that form an electrode array 17. For example, one or more percutaneous leads 15 can be used having ring-shaped or split-ring electrodes 16 carried on a flexible body 18. In another example, a paddle lead 19 provides electrodes 16 positioned on one of its generally flat surfaces. Lead wires 20 within the leads are coupled to the electrodes 16 and to proximal contacts 21 insertable into lead connectors 22 fixed in a header 23 on the IPG 10, which header can comprise an epoxy for example. Once inserted, the proximal contacts 21 connect to header contacts 24 within the lead connectors 22, which are in turn coupled by feedthrough pins 25 through a case feedthrough 26 to stimulation circuitry 28 within the case 12.

In the illustrated IPG 10, there are thirty-two electrodes (E1-E32), split between four percutaneous leads 15, or contained on a single paddle lead 19, and thus the header 23 may include a 2×2 array of eight-electrode lead connectors 22. However, the type and number of leads, and the number of electrodes, in an IPG is application specific and therefore can vary. The conductive case 12 can also comprise an electrode (Ec). In a SCS application, the electrode lead(s) are typically implanted in the spinal column proximate to the dura in a patient's spinal cord, preferably spanning left and right of the patient's spinal column. The proximal contacts 21 are tunneled through the patient's tissue to a distant location such as the buttocks where the IPG case 12 is implanted, at which point they are coupled to the lead connectors 22. In other IPG examples designed for implantation directly at a site requiring stimulation, the IPG can be lead-less, having electrodes 16 instead appearing on the body of the IPG 10 for contacting the patient's tissue. The IPG lead(s) can be integrated with and permanently connected to the IPG 10 in other solutions. The goal of SCS therapy is to provide electrical stimulation from the electrodes 16 to alleviate a patient's symptoms, such as chronic back pain.

IPG 10 can include an antenna 27a allowing it to communicate bi-directionally with a number of external devices discussed subsequently. Antenna 27a as shown comprises a conductive coil within the case 12, although the coil antenna 27a can also appear in the header 23. When antenna 27a is configured as a coil, communication with external devices preferably occurs using near-field magnetic induction. IPG 10 may also include a Radio-Frequency (RF) antenna 27b. In FIG. 1, RF antenna 27b is shown within the header 23, but it may also be within the case 12. RF antenna 27b may comprise a patch, slot, or wire, and may operate as a monopole or dipole. RF antenna 27b preferably communicates using far-field electromagnetic waves, and may operate in accordance with any number of known RF communication standards, such as Bluetooth™, Zigbee™, WiFi™, MICS™, and the like.

Stimulation in IPG 10 is typically provided by pulses each of which may include a number of phases such as 30a and 30b, as shown in the example of FIG. 2. Stimulation parameters typically include amplitude (current I, although a voltage amplitude V can also be used); pulse frequency (F); pulse width (PW) of the pulses or of its individual phases such as 30a and 30b; the electrodes 16 selected in the array 17 to provide the stimulation; and the polarity of such selected electrodes, i.e., whether they act as anodes that source current to the tissue or cathodes that sink current from the tissue. These and possibly other stimulation parameters taken together comprise a stimulation program that the stimulation circuitry 28 in the IPG 10 can execute to provide therapeutic stimulation to a patient. Examples of stimulation circuitry 28 useable in an IPG 10 are discussed later. IPG 10, and stimulator devices more generally, should be understood including stimulation devices having stimulation circuitries such as External Trial Stimulators (ETSs), which are connected to implanted leads 15 and allow stimulation to be tried on a trial basis before implantation of the IPG 10. See, e.g., U.S. Pat. Nos. 9,724,508 and 9,259,574 (explaining ETSs).

In the example of FIG. 2, electrode E1 has been selected as an anode (during its first phase 30a), and thus provides pulses which source a positive current of amplitude +I to the tissue. Electrode E2 has been selected as a cathode (again during first phase 30a), and thus provides pulses which sink a corresponding negative current of amplitude –I from the tissue. This is an example of bipolar stimulation, in which only lead-based electrodes are used to provide stimulation to the tissue (one anode pole, one cathode pole). However, more than one electrode may be selected to provide an anode pole at a given time, and more than one electrode may be selected to act as a cathode to provide a cathode pole at a given time, as explained further below. The IPG 10 can typically also provide monopolar stimulation, where the case electrode Ec is selected as a return electrode.

The stimulation pulses shown in FIG. 2 are biphasic, with each pulse comprising a first phase 30a followed thereafter by a second phase 30b of opposite polarity. Biphasic pulses are useful to actively recover any charge that might be stored on capacitive elements in the electrode current paths, such as on the DC-blocking capacitors 38 present in the stimulation circuitry 28 (see FIG. 5). See also U.S. Patent Application Publication 2020/0305745 (discussing active charge recovery and biphasic pulses). Passive charge recovery can also occur after the active pulse phases, such as during durations 30c. Currents are not actively driven by the stimulation circuitry 28 during passive charge recovery, and instead various switches are closed to effectively short the electrodes together to passively recover stored charge. See, e.g., U.S. Pat. Nos. 10,716,937 and 10,792,491 (discussing passive charge recovery).

FIG. 3 shows various external systems 40, 50, and 60 that can wirelessly communicate data with the IPG 10 (which again can include an ETS). Such systems can be used to wirelessly transmit a stimulation program to the IPG 10—that is, to program its stimulation circuitry 28 to produce stimulation with desired amplitudes and timings as described earlier. Such systems may also be used to adjust one or more stimulation parameters of a stimulation program that the IPG 10 is currently executing, and/or to wirelessly receive information from the IPG 10, such as various status information, etc.

External controller 40 can be as described in U.S. Patent Application Publication 2015/0080982 for example, and may comprise a portable, hand-held controller dedicated to work with the IPG 10. External controller 40 may also comprise a general-purpose mobile electronics device such as a mobile phone which has been programmed with a Medical Device Application (MDA) allowing it to work as a wireless controller for the IPG 10, as described in U.S. Patent Application Publication 2015/0231402. External controller 40 includes a display 41 and a means for entering commands, such as buttons 42 or selectable graphical icons provided on the display 41. The external controller 40's user interface enables a patient to adjust stimulation parameters, although it may have limited functionality when compared systems 50 and 60, described shortly. The external controller 40 can have one or more antennas capable of communicating with the IPG 10. For example, the external controller 40 can have a near-field magnetic-induction coil antenna 44a capable of wirelessly communicating with the coil antenna 27a in the IPG 10. The external controller 40 can also have a far-field RF antenna 44b capable of wirelessly communicating with the RF antenna 27b in the IPG 10.

Clinician programmer 50 is described further in U.S. Patent Application Publication 2015/0360038, and can comprise a computing device such as a desktop, laptop, or notebook computer, a tablet, a mobile smart phone, a Personal Data Assistant (PDA)-type mobile computing device, etc. In FIG. 3, the computing device is shown as a laptop computer that includes typical computer user interface means such as a display 51, buttons 52, as well as other user-interface devices such as a mouse, a keyboard, speakers, a stylus, a printer, etc., not all of which are shown for convenience. Also shown in FIG. 3 are accessory devices for the clinician programmer 50 that are usually specific to its operation as a stimulation controller, such as a communication "wand" 56 coupleable to suitable ports on the computing device. The antenna used in the clinician programmer 50 to communicate with the IPG 10 can depend on the type of antennas included in the IPG 10. If the patient's IPG 10 includes a coil antenna 27a, wand 56 can likewise include a coil antenna 54a to establish near-field magnetic-induction communications at small distances. In this instance, the wand 56 may be affixed in close proximity to the patient, such as by placing the wand 56 in a belt or holster wearable by the patient and proximate to the patient's IPG 10. If the IPG 10 includes an RF antenna 27b, the wand 56, the computing device, or both, can likewise include an RF antenna 54b to establish communication with the IPG 10 at larger distances. The clinician programmer 50 can also communicate with other devices and networks, such as the Internet, either wirelessly or via a wired link provided at an Ethernet or network port.

External system 60 comprises another means of communicating with and controlling the IPG 10 via a network 65 which can include the Internet. The network 65 can include a server 66 programmed with communication and control functionality, and may include other communication networks or links such as WiFi™, cellular or land-line phone links, etc. The network 65 ultimately connects to an intermediary device 62 having antennas suitable for communication with the IPG's antenna, such as a near-field magnetic-induction coil antenna 64a and/or a far-field RF antenna 64b. Intermediary device 62 may be located generally proximate to the IPG 10. Network 65 can be accessed by any user terminal 70, which typically comprises a computer device associated with a display 71. External system 60 allows a remote user at terminal 70 to communicate with and control the IPG 10 via the intermediary device.

FIG. 3 also shows circuitry 80 involved in any of external systems 40, 50, or 60. Such circuitry can include control circuitry 82, which can comprise any number of devices such as one or more microprocessors, microcomputers, FPGAs, DSPs, other digital logic structures, etc., which are capable of executing programs in a computing device. Such control circuitry 82 may contain or coupled with memory 84 which can store external system software 86 for controlling and communicating with the IPG 10, and for rendering a Graphical User Interface (GUI) 90 on a display (41, 51, 71) associated with the external system. In external system 60, the external system software 86 would likely reside in the server 66, while the control circuitry 82 could be present in either or both the server 66 or the terminal 70.

An example of GUI 90 renderable on an external system is shown in FIG. 4. One skilled in the art will understand that the particulars of the GUI 90 will depend on where external system software 86 is in its execution, which may depend on previous GUI selections the clinician has made. FIG. 4 shows the GUI 90 at a point allowing for the setting of stimulation parameters for the patient and for their storage as a stimulation program. To the left a program interface 91 is shown, which allows for naming, loading and saving of stimulation programs for the patient. Shown to the right is a stimulation parameters interface 92, in which specific stimulation parameters can be defined for a stimulation program. Values for stimulation parameters relating to the shape of the waveform (I; in this example, current), pulse width (PW, of either or both phases 30a and 30b), and frequency (F) are shown in a waveform parameter interface 93, including buttons the clinician can use to increase or decrease these values.

Stimulation parameters relating to the electrodes 16 that will receive the defined waveform are selectable in an electrode parameter interface 94. (As discussed shortly, electrode stimulation parameters may also be determined automatically by an electrode configuration algorithm operable in the external system software 86). The electrode parameter interface 94 allows different electrodes (including case electrode Ec) to be selected to receive stimulation, and to define the polarity of those electrodes (anode, cathode, off). The electrode parameter interface 94 further allows the relative percentage (X %) of the prescribed amplitude I to be defined at each electrode. This is particularly useful if the anodic or cathodic current is to be shared by more than one electrode at any given time: for example, if anode E1 receives 80%*+I and anode E2 receives 20%*+I; or if cathode E11 receives 30%*–I, cathode E12 receives 50%*–I, and cathode E6 receives 20%*–I. Such sharing of anodic (+I) and cathodic (–I) currents allows anode and cathode poles 93 to be formed whose positions in the electrode array 17 do not necessarily correspond to the physical positions of any particular electrode 16.

A leads interface 95 can display the various leads 15, or the electrode array 17 more generally, with the electrodes shown in proper position with respect to each other, for example, on the left and right sides of the spinal column. Anode (+) and cathode (–) poles 93 indicative of the specification stimulation may also be displayed in the leads interface 95 at a proper location in the electrode array 17. The position of these poles 93 may be set in accordance with the above-mentioned electrode configuration algorithm, which allows a position of a pole 93 to be determined from the active electrodes, their polarities, and their relative percentages. See U.S. Pat. No. 10,881,859 (discussing an electrode configuration algorithm). A cursor 96 (or other selection means such as a mouse pointer) can be used to move the poles 93 in the electrode array 17; to select particular electrodes or positions in the leads interface 95; and/or to otherwise navigate the GUI 90. The electrode configuration algorithm may operate in reverse to determine which electrodes to activate, and with which polarities and relative percentages, when the position of the one or more poles 93 is set or moved in the leads interface 95. The stimulation (i.e., poles 93) may also be moved in the electrode array using other GUI elements, such as direction arrows 97.

An advanced menu 98 can also be used (among other things) to define the relative durations and amplitudes of the pulse phases 30a and 30b, and to allow for other more advanced modifications, such as setting burst of pulses, setting a duty cycle (on/off time) for the stimulation pulses, and setting a ramp-up time over which stimulation reaches its programmed amplitude (I), etc. A mode menu 99 allows the clinician to choose different modes for determining stimulation parameters.

SUMMARY

A method is disclosed for calibrating stimulation circuitry in a stimulator device comprising a plurality of electrodes configured to contact a tissue of a patient, wherein the stimulation circuitry is controllable to control an amplitude of stimulation at a selected one or more of the plurality of electrodes. The method may comprise: measuring a neural response to stimulation provided at the selected one or more of the electrodes; determining information indicative of a window of amplitudes from the measured neural response; and programming the stimulation circuitry with the information to constrain control of the amplitude of the stimulation at the selected one or more of the electrodes to within the window of amplitudes.

In one example, determining the information indicative of the window of amplitudes from the measured neural response comprises: determining one or more neural response features for the measured neural response; and determining the information indicative of the window of amplitudes from the one or more neural response features. In one example, the one or more neural response features comprises a feature indicative of the size or shape of the measured neural response. In one example, the one or more neural response features comprises a neural response amplitude. In one example, the one or more neural response features comprises an Extracted Neural Threshold (ENT), wherein the ENT comprises a lowest amplitude of the stimulation provided at the selected one or more of the electrodes at which a neural response can be detected. In one example, the information indicative of the window of amplitudes comprises a minimum amplitude and a maximum amplitude. In one example, the information indicative of the window of amplitudes comprises information from which a minimum amplitude and a maximum amplitude can be ascertained. In one example, the stimulation circuitry is controllable by an amplitude bus configured to carry a plurality of amplitude values to control the amplitude of the stimulation. In one example, the window of amplitudes comprises a minimum amplitude and a maximum amplitude, and wherein all of the plurality of amplitude values are used to set the stimulation at the selected one or more of the electrodes to within the window of amplitudes. In one example, the stimulation circuitry is capable of producing a range of amplitudes of the stimulation, and wherein the window of amplitudes is within and smaller than the range of amplitudes. In one example, the neural response is measured at one or more of the electrodes different from the selected one or more of the electrodes that provide the stimulation. In one example, the stimulator device comprises a spinal cord stimulator. In one example, the neural response comprises an Evoked Compound Action Potential (ECAP). In one example, the method is performed periodically. In one example, the method is performed periodically within the stimulator device.

A system is disclosed, which may comprise: a stimulator device comprising: a plurality of electrodes configured to contact a tissue of a patient; stimulation circuitry configured to control an amplitude of stimulation at a selected one or more of the plurality of electrodes; control circuitry configured to: measure a neural response to stimulation provided at the selected one or more of the electrodes, receive information indicative of a window of amplitudes determined from the measured neural response, and program the stimulation circuitry with the information to constrain control of the amplitude of the stimulation at the selected one or more of the electrodes to within the window of amplitudes.

In one example, the control circuitry is further configured to determine the information indicative of the window of amplitudes from the measured neural response. In one example, the control circuitry is configured to determine the information indicative of the window of amplitudes from the measured neural response by determining one or more neural response features for the measured neural response; and determining the information indicative of the window of amplitudes from the one or more neural response features. In one example, the one or more neural response features comprises a feature indicative of the size or shape of the measured neural response. In one example, the one or more neural response features comprises a neural response amplitude. In one example, the one or more neural response features comprises an Extracted Neural Threshold (ENT), wherein the ENT comprises a lowest amplitude of the stimulation provided at the selected one or more of the electrodes at which a neural response can be detected. In one example, the information indicative of the window of amplitudes comprises a minimum amplitude and a maximum amplitude. In one example, the information indicative of the window of amplitudes comprises information from which a minimum amplitude and a maximum amplitude can be ascertained. In one example, the stimulation circuitry is controllable by an amplitude bus configured to carry a plurality of amplitude values to control the amplitude of the stimulation. In one example, the window of amplitudes comprises a minimum amplitude and a maximum amplitude, and wherein all the plurality of amplitude values are used to set the stimulation at the selected one or more of the electrodes to within the window of amplitudes. In one example, the stimulation circuitry is capable of producing a range of amplitudes of the stimulation, and wherein the window of amplitudes is within and smaller than the range of amplitudes. In one example, the neural response is measured at one or more of the electrodes different from the selected one or more of the electrodes that provide the stimulation. In one example, the stimulator device comprises a spinal cord stimulator. In one example, the neural response comprises an Evoked Compound Action Potential (ECAP). In one example, the system further comprises an external system in communication with the stimulator device. In one example, the external system is configured to receive information indicative of the measured neural response from the stimulator device, determine the information indicative of the window of amplitudes from the received information indicative of the measured neural response, and transmit the information indicative of the window of amplitudes to the stimulator device. In one example, the external system comprises an external controller or a clinician programmer.

BRIEF DESCRIPTION OF THE DRAWINGS

FIGS. 9A-9D show a first example of stimulation circuitry that can be programmed with therapeutic window information determined from neural response sensing. Beneficially, the digital amplitude values are not limited despite operation being constrained to the therapeutic window, which allows the adjustment of the amplitude within the therapeutic window in smaller current increments.

DETAILED DESCRIPTION

An increasingly interesting development in pulse generator systems, and in Spinal Cord Stimulator (SCS) pulse generator systems specifically, is the addition of sensing capability to complement the stimulation that such systems provide. For example, and as explained in U.S. Patent Application Publication 2017/0296823, it can be beneficial to sense a neural response in neural tissue that has received Spinal Cord Stimulation from an IPG. Sensing a neural response can be useful in other contexts as well, such as in Deep Brain Stimulation, as discussed in U.S. Patent Application Publication 2022/0040486.

Figures 5, 6:
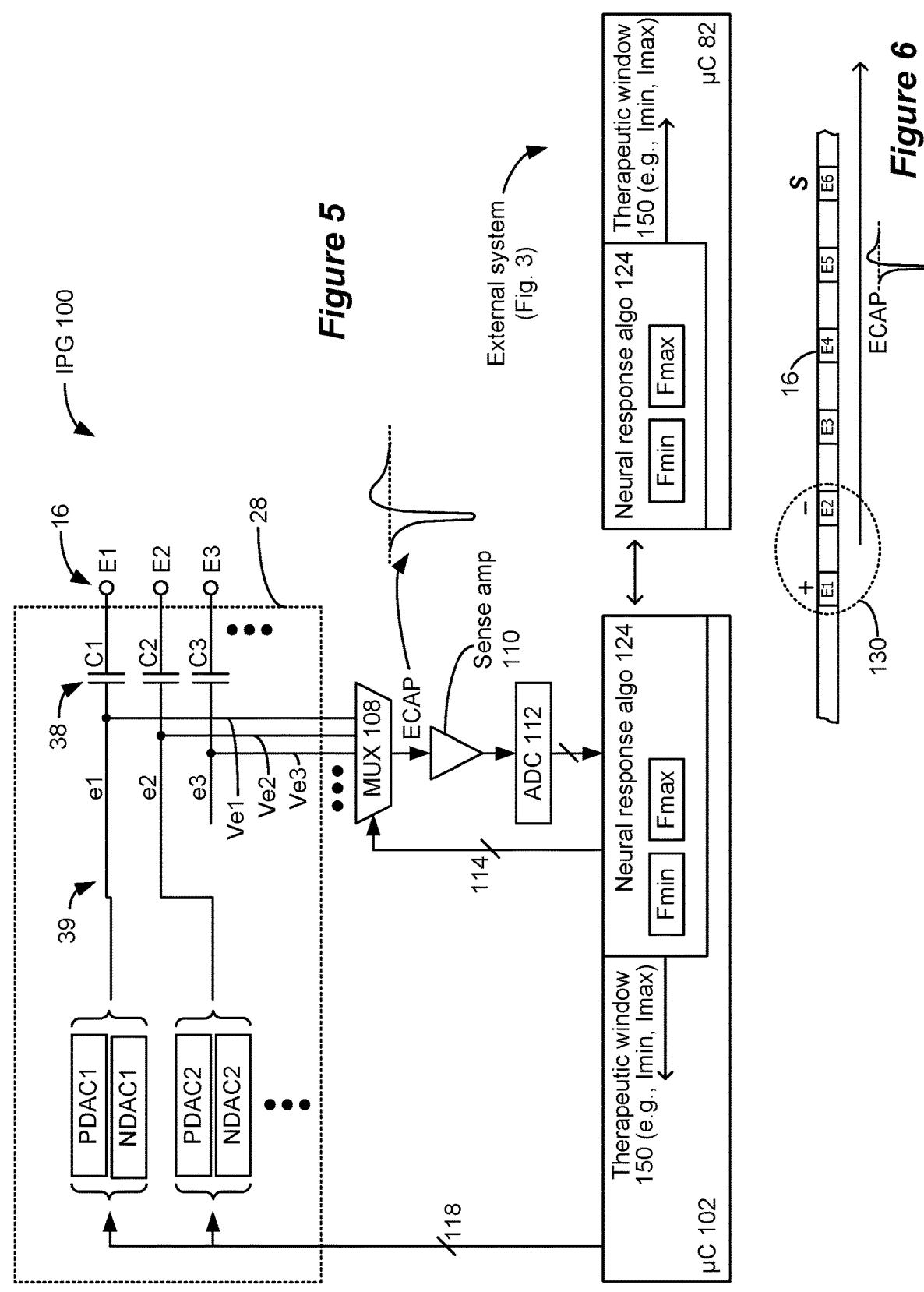
FIG. 5 shows an improved IPG having neural response sensing, and the ability to adjust stimulation dependent on such sensing.
FIG. 6 shows stimulation producing a neural response, and the sensing of that neural response at at least one electrode of the IPG.

FIG. 5 shows circuitry for an IPG 100 having neural response sensing capability. The IPG 100 includes control circuitry 102, which may comprise a microcontroller for example, such as Part Number MSP430, manufactured by Texas Instruments, which is described in data sheets at on that company's website. Other types of control circuitry may be used in lieu of a microcontroller as well, such as microprocessors, FPGAs, DSPs, or combinations of these, etc. Control circuitry 102 may also be formed in whole or in part in one or more Application Specific Integrated Circuits (ASICs) in the IPG 100, which ASIC(s) may additionally include the other circuitry shown in FIG. 5.

FIG. 5 includes the stimulation circuitry 28 described earlier, which includes digital-to-analog converter (DAC) circuitry used to produce currents at the electrodes. The DAC circuitry is divided into PDACs (Positive DACs) that can source (positive) currents to selected (anode) electrodes, and NDACs (Negative DACs) that can sink (negative) currents from selected (cathode) electrodes. In the example shown, a PDAC/NDAC pair is dedicated to each electrode, with PDAC1/NDAC1 able to provide anodic/cathodic currents to E1, PDAC2/NDAC2 able to provide anodic/cathodic currents to E2, etc. However, this is just one example, and other examples of stimulation circuitries useable in IPGs 100 are disclosed in U.S. Pat. Nos. 8,606,362; 8,620,436; 10,525,253; 11,040,192; 10,912,942; and U.S. Patent Application Publications 2021/0275798; and 2022/0321139. A bus 118 provides digital control signals to the stimulation circuitry 28 to produce currents or voltages of prescribed amplitudes (I) and with the correct timing (PW, F) at the electrodes selected for stimulation. The electrode current paths to the electrodes 16 include the DC-blocking capacitors 38 described earlier, each of which separates an electrode node 39 (ei) at the output of the PDAC/NDAC pairs from the electrodes 16 (Ei) that contact the tissue.

The control circuitry 102 can be programmed with a neural response algorithm 124 to evaluate a neural response of neurons that "fire" (are recruited) in response to the stimulation that the IPG 100 provides. One such neural response depicted in FIGS. 5 and 6 is an Evoked Compound Action Potential, or "ECAP," although other types of neural responses also exist and can be sensed by the IPG 100. As its name implies, an ECAP comprises a compound (summation) of various action potentials issued from a plurality of recruited neurons, and its amplitude and shape varies depending on the number and type of neural fibers that are firing. Generally speaking, an ECAP can vary between tens of microVolts to tens of milliVolts. The neural response algorithm 124 assesses the ECAP and can, for example, adjust the stimulation program in a closed loop fashion via bus 118. In this regard, the neural response algorithm 124 can attempt to remove other signals that may be present in the tissue (stimulation artifacts, background signals and noise, etc.) and determine one of more features indicative of the size and shape of the ECAP (e.g., peak-to-peak heights, peak areas, line lengths, etc.). Such ECAP features are described in further details in U.S. Patent Application Publication 2020/0305744, which is incorporated herein by reference in its entirety.

Figure 1:
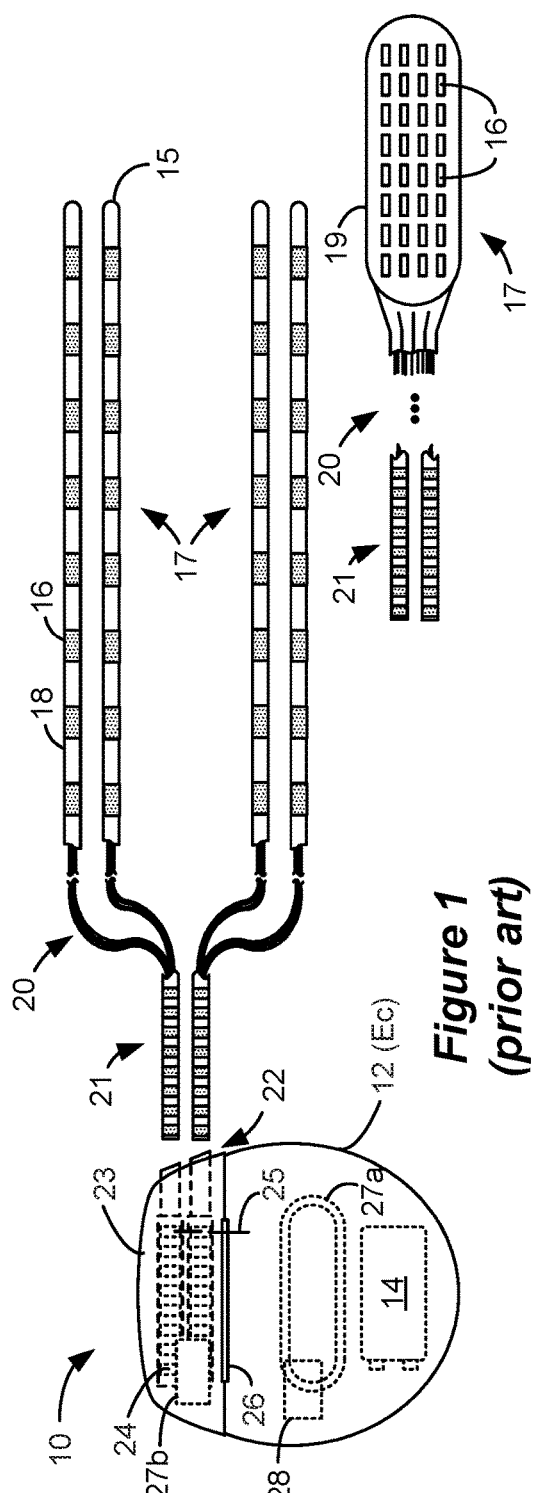
FIG. 1 shows an Implantable Pulse Generator (IPG), in accordance with the prior art.
Figure 2:
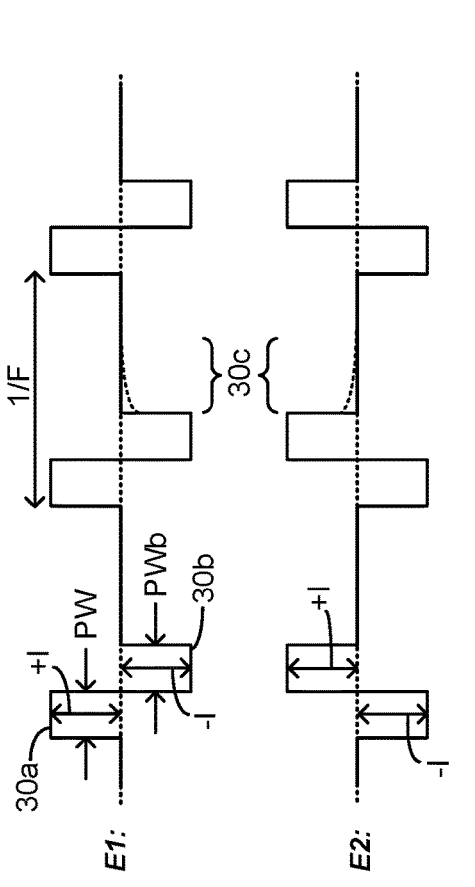
FIG. 2 shows an example of stimulation pulses producible by the IPG, in accordance with the prior art.
Figure 3:
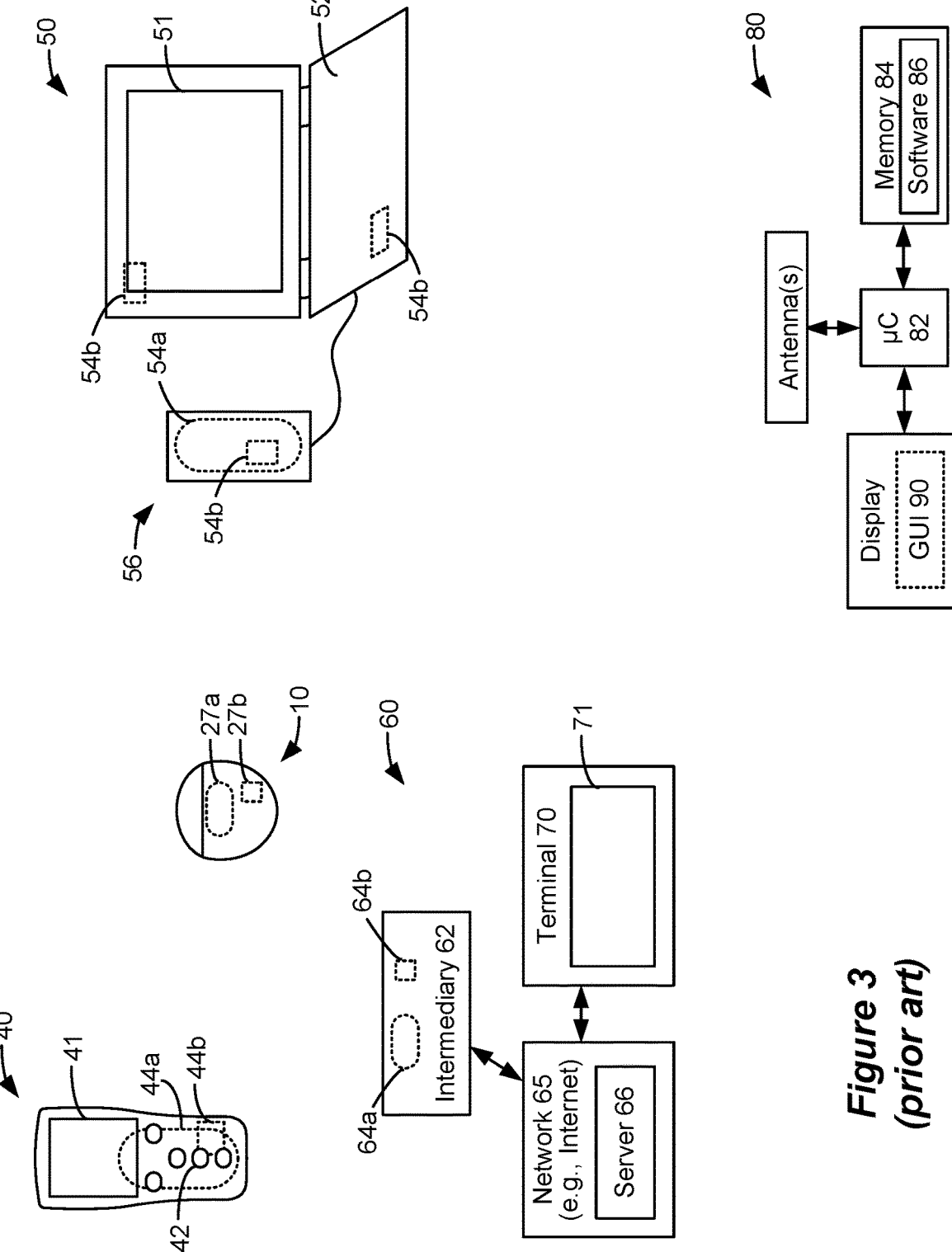
FIG. 3 shows various external systems capable of communicating with and programming stimulation in an IPG, in accordance with the prior art.
Figure 4:
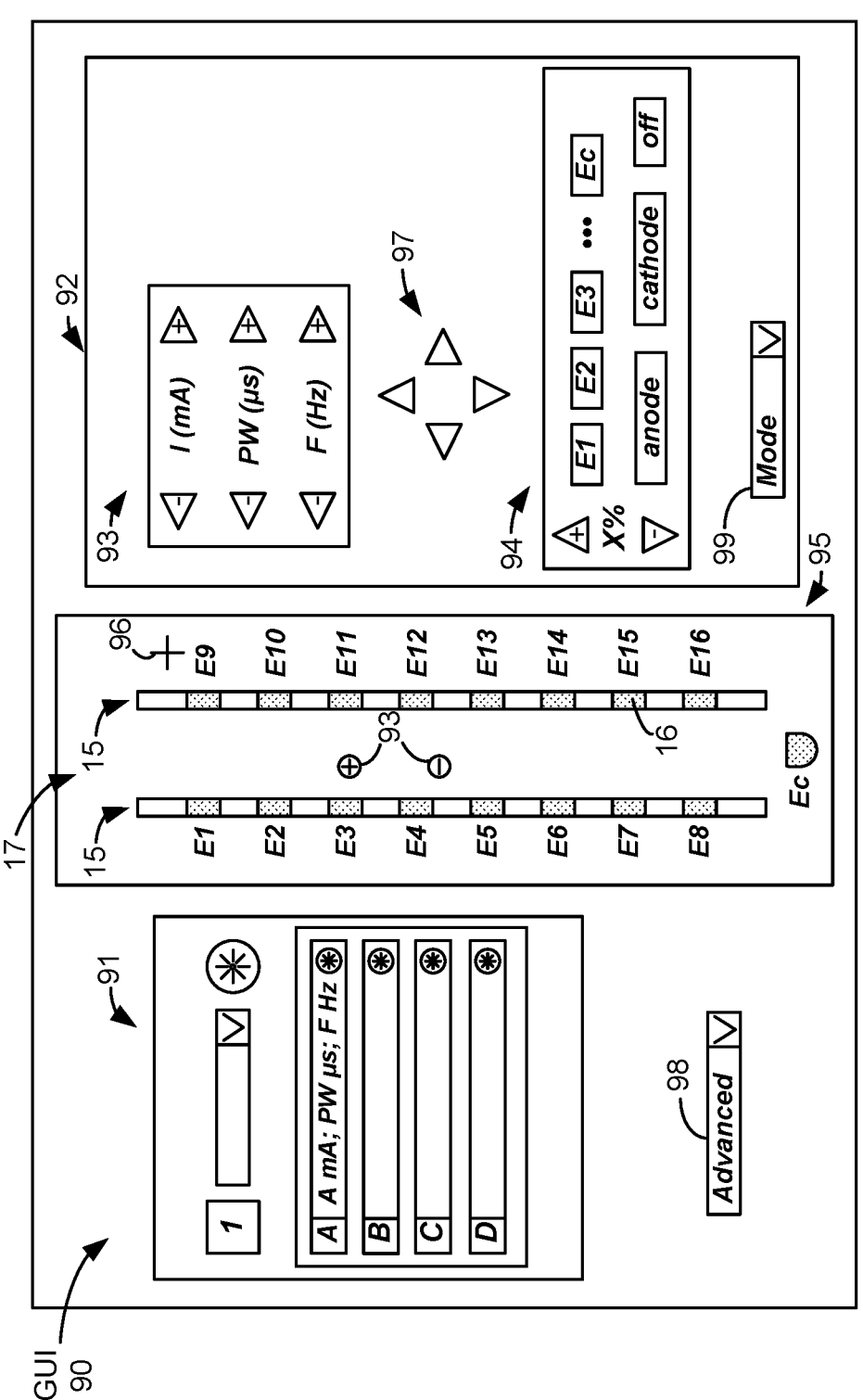
FIG. 4 shows a Graphical User Interface (GUI) of an external device such as a clinician programmer, in accordance with the prior art.

The control circuitry 102 and/or the neural response algorithm 124 can also enable one or more of the electrodes 16 to act as a sense electrode (S) to sense the ECAP, either automatically or based on a user selection of the sense electrode(s) as entered into an external system via GUI 90 for example (see FIGS. 3 & 4). As shown in FIG. 6, the ECAP will be initiated upon stimulation of neural fibers in a recruited neural population 130 proximate to the electrodes chosen for stimulation (e.g., E1 and E2), and will move through the patient's tissue (e.g., the spinal cord) via neural conduction. In the simple example of FIG. 6, electrode E6 is chosen as a sense electrode S, and thus this electrode will detect the ECAP as it moves past. The speed at which the ECAP moves depends on several factors.

To assist with selection of the sensing electrode(s), and referring again to FIG. 5, each electrode node ei 39 is made coupleable to at least one sense amp 110. In this example, for simplicity, all of the electrode nodes are shown as sharing a single sense amp 110. Thus, any sensing electrode (e.g., electrode node e6) can be coupled to the sense amp 110 (e.g., Ve6) at a given time per multiplexer 108, as controlled by bus 114. Although not shown, each electrode node can also be coupleable to its own dedicated sense amp 110. ECAP sensing can also involve differential sensing of the ECAP at more than one electrode (e.g., at electrodes E5 and E6), and thus two electrode nodes (e.g., Ve5 and Ve6) can be selected by multiplexer 108 and input to a differential sense amp 110, as explained for example in U.S. Patent Application Publication 2020/0305744. After the ECAP is sensed, the analog waveform comprising the ECAP is preferably converted to digital signals by an Analog-to-Digital converter 112, which may also reside within the control circuitry 102. The neural response algorithm 124 can then assess the size and shape of the ECAP (e.g., determine one or more ECAP features as already described), and if necessary, make adjustments to stimulation via bus 118.

In an alternative, the neural response algorithm 124 may also operate wholly or at least partially in external systems in communication with the IPG 100, as discussed earlier with respect to FIG. 3. In this alternative, the portion of algorithm 124 operating in the external system can perform signal processing and feature extraction. For example, the IPG 100 can transmit to the external system representations of the sensed neural responses, leaving algorithm 124 in the external system to determine ECAP features from these responses. The algorithm 124 may also cause the IPG 100 to transmit determined ECAP features to the external system for analysis and/or action such as stimulation adjustment (e.g., via bus 118). When algorithm 124 operates at least in part in an external system, the algorithm 124 can comprise part of clinician programmer software 86 as executed by control circuitry 82 (FIG. 3).

Figure 7A:
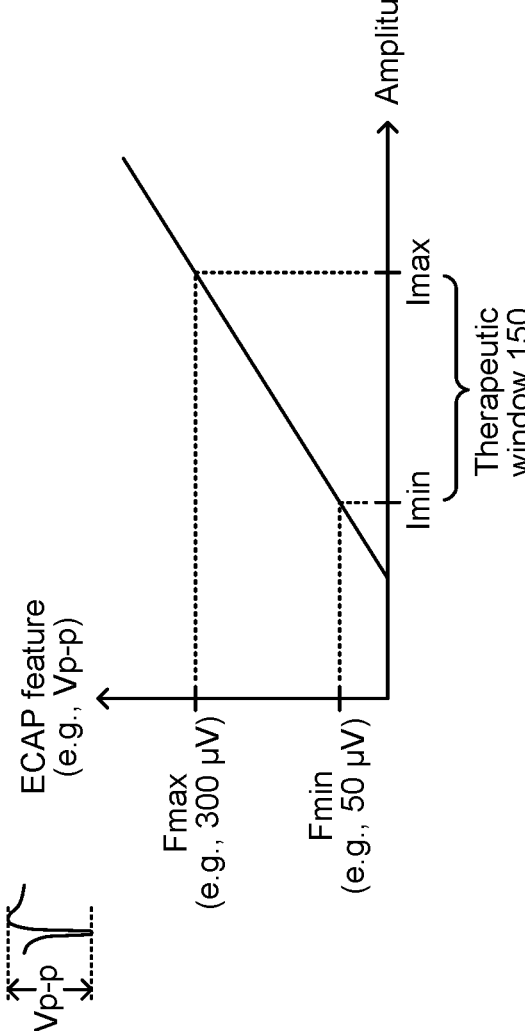
FIGS. 7A and 7B show how a therapeutic window of stimulation amplitude can be determined using measured neural responses.

As noted above, the neural response algorithm 124 can be used to adjust a stimulation program (e.g., via bus 118), and in particular can be used to set or adjust the amplitude I of the stimulation. For example, FIG. 7A shows a graph of a neural response feature that the algorithm 124 can determine. As discussed above, the algorithm 124 can determine a number of such features, but in FIG. 7A it is assumed that a peak-to-peak voltage (Vp-p) feature of an ECAP is determined, which generally indicates an amplitude of the neural response. This feature is determined as a function of the stimulation amplitude I, and in this regard the algorithm 124 measures Vp-p as it gradually increases the amplitude I (via bus 118).

The algorithm 124 can also determine, or be programmed with, minimum and maximum values for the neural response feature in question (e.g., Fmin=50 μV and Fmax=300 μV). See FIG. 5. These maximum and minimum features may be known or determined to be beneficial for the patient, perhaps on the basis of other information the algorithm 124 receives. For example, the algorithm 124 may determine or be programmed to understand that the stimulation therapy is effective if the value of the feature is at or between Fmin and Fmax. In this regard, it may be known or determinable that if the value of the neural feature is less than Fmin, the patient is not receiving substantial benefit from the stimulation therapy (e.g., insubstantial pain reduction). Similarly, it may be known or determinable that if the value of the feature is greater than Fmax, the stimulation therapy isn't effective, perhaps because it causes patient discomfort.

Because the magnitude of ECAP features generally correlates with the amplitude of the current I as the graph in FIG. 7A shows, these minimum and maximum ECAP features Fmin and Fmax can be correlated by the algorithm 124 to minimum and maximum currents amplitudes, Imin and Imax, for a given patient. Algorithm 124 may therefore automatically determine Imin and Imax based on Fmin and Fmax. Algorithm 124 may also determine Imin and Imax based on input from a clinician (e.g., on an external system) upon reviewing the ECAP responses. In other words, a clinician may determine Imin and Imax for the algorithm 124 in light of the neural response that the clinician reviews.

Once Imin and Imax are determined using the measured neural responses, they can be used to adjust the stimulation that the patient receives. For example, the stimulation amplitude I may be constrained to values between and including Imin and Imax—i.e., to amplitude values within a therapeutic window 150—because it is known that the current at these amplitudes provides a desired and therapeutically effective neural response. In short, algorithm 124, whether running on external systems and/or the IPG 100, may determine information indicative of therapeutic amplitude window 150. Such information (e.g., Imin, Imax) may be sent to the stimulation circuitry 28 in the IPG (e.g., via bus 118) to constrain the stimulation therapy that the patient receives, as shown in FIG. 5.

Figure 7B:
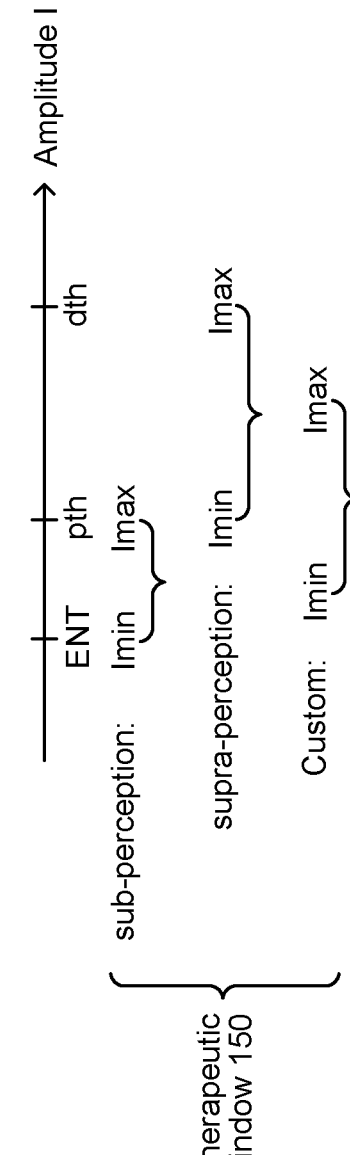

FIG. 7B shows another manner in which therapeutic amplitude windows 150 can be determined for a patient using measured neural responses. FIG. 7B relies on concepts taught in U.S. patent application Publication 2022/0305269, which is incorporated herein by reference in its entirety. As disclosed in the '269 Publication, stimulation can be provided with reference to a number of different physiological thresholds that cause physiological responses in the patient. FIG. 7B shows an example of two particular physiological thresholds, which are called the perception threshold (pth) and the discomfort threshold (dth). Other physiological thresholds also exist, but are not shown for simplicity. Such physiological thresholds may be expressed in terms of current amplitude I of the stimulation therapy that is provided to the patient, although other parameters of the stimulation therapy (e.g., pulse width, frequency) could be used to define these thresholds as well. The perception threshold pth comprises a lowest amplitude at which the patient can still feel the stimulation (as paresthesia), or as a highest amplitude at which the patient cannot feel the stimulation. As such, the perception threshold pth demarks a boundary between sub-perception stimulation therapy (I<pth) and supra-perception stimulation therapy (I>pth). The discomfort threshold dth comprises a highest amplitude at which stimulation is still comfortable for the patient. In other words, stimulation amplitudes above dth (I>dth) are uncomfortable for the patient, and thus these higher amplitudes are generally avoided.

The '269 Publication teaches that it can be useful to determine an Extracted Neural Threshold (ENT). Determining an ENT involves sensing a neural response to stimulation, and so can also involve use of neural response algorithm 124. An ENT, like the physiological thresholds discussed above, may be expressed in terms of a current amplitude I of the stimulation therapy that is provided to the patient, and specifically can comprise the minimum amplitude at which a neural response such as an ECAP can be reliably detected, or the maximum amplitude at which no neural response is reliably detected. The neural response algorithm 124 can thus operate to determine ENT for a given stimulation program by increasing the amplitude I to a point where an ECAP is detectable by the algorithm 124, or by decreasing the amplitude to a point where an ECAP is no longer detectable. As explained in the '269 Publication, an ENT is not an absolute value, because a value for ENT in a given system can depend on how readily the system can determine the presence of a neural response. This can depend for example on the sensitivity of the sense amp circuitry 110, the algorithm 124's ability to disclude from the sensed neural signal other aspects like stimulation artifacts, etc. In FIG. 7B, it is assumed that ENT values are lower than the perception threshold values pth. However, in embodiments where the sense amp circuit 110 or the algorithm 124 are less capable, the ENT resolvable by the system may be higher than pth. An ENT value can comprise a neural response feature.

The '269 Publication teaches that physiological thresholds (e.g., pth and/or dth) can be predicted once the ENT is determined using mathematical relationships as disclosed in that application. Once these thresholds (ENT, pth, dth) are established, they may be used by the neural response algorithm 124 to define therapeutic amplitude windows 150, and different examples are shown in FIG. 7B. For example, and assuming that ENT <pth, sub-perception stimulation therapy can be provided by measuring ENT from neural responses; setting Imin to ENT; predicting pth from ENT; and setting pth to Imax. Although not shown in FIG. 7B, if ENT is higher than pth, then sub-perception could be provided by measuring ENT from neural responses; predicting pth from ENT; setting Imax to pth, and setting Imin to a value below pth (such as 0 mA). Supra-perception stimulation therapy can be provided by measuring ENT from neural responses; predicting pth and dth from ENT; setting Imin to pth; and setting dth to Imax, as shown in FIG. 7B. Algorithm 124 may also set a custom therapeutic window, in which Imin and Imax are set based on ENT, but where Imin and Imax are not necessarily tied to physiological thresholds such as pth and dth, as also shown in FIG. 7B.

In summary, neural responses can be measured (e.g., features, ENT values, etc.) and used to set a therapeutic window 150 of a stimulation parameter such as amplitude I for the patient. More broadly, neural response measurements may only cause a lower or upper limit of a therapeutic window (Imin or Imax) to be set: there may be no opposing upper or lower limit, or such opposing other limit may be predicted or set in other manners. For example, Imin may be determined based on neural response measurements, and Imax may be set as a maximum amplitude (e.g., 25.5 mA) the IPG 100 can provide. Or, Imax may be determined based on neural response measurements, and Imin set at a minimum amplitude (e.g., 0 mA) the IPG 100 can provide.

Regardless of how a therapeutic window 150 for a stimulation parameter such as amplitude is determined or set for a patient using neural response measurements, the stimulation provided to the patient may be constrained with that window. For example, the IPG 100, and/or the external system (its GUI 90) may be programmed to prohibit the selection of an amplitude greater than Imax, or less than Imin, because such values will not be expected to be therapeutically useful for the patient.

Figure 8:
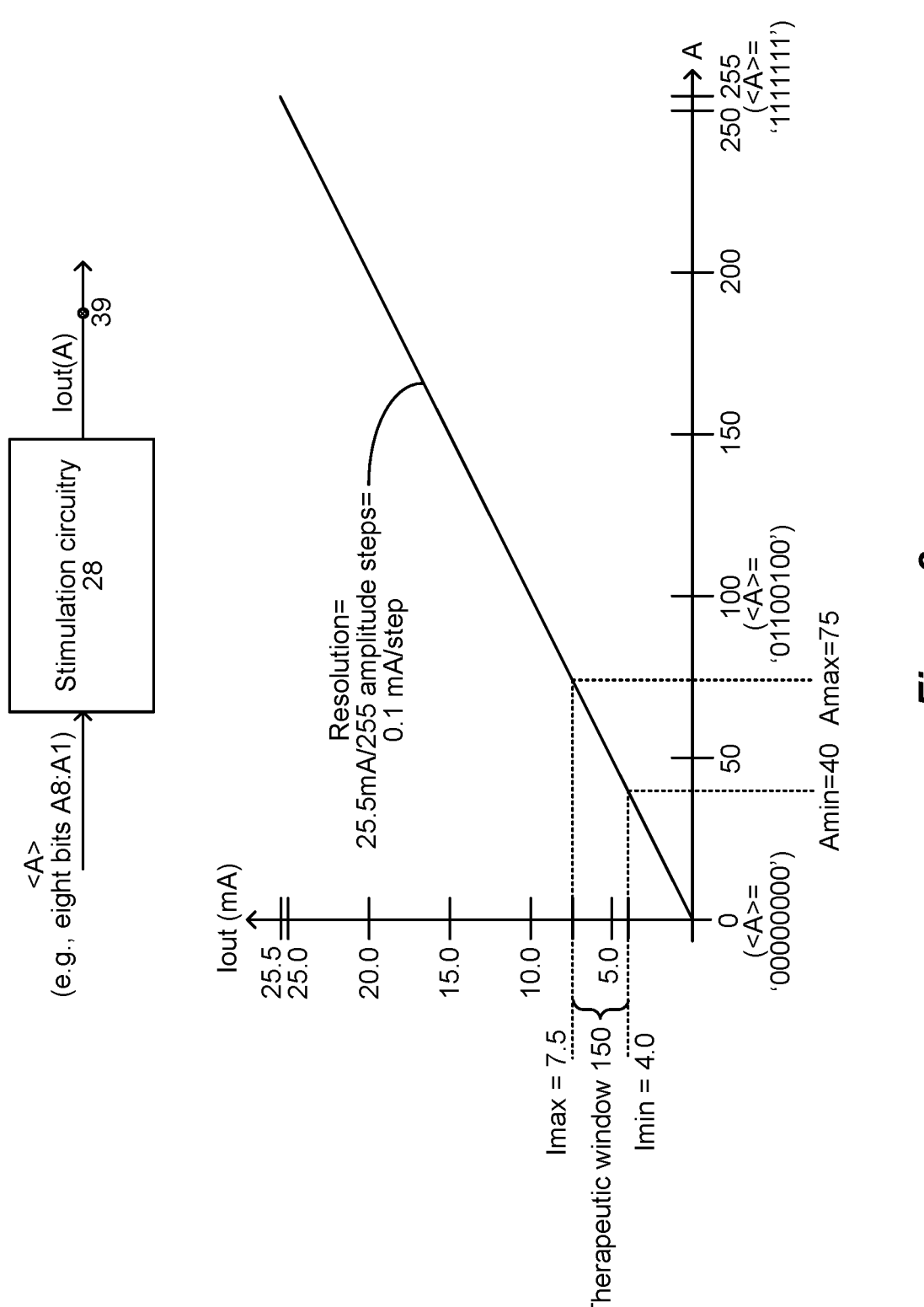
FIG. 8 shows operation of traditional stimulation circuitry when operation is constrained to a therapeutic amplitude window, and shows limitation of the digital amplitude values that the DAC can otherwise handle.

However, limiting a stimulation parameter to a therapeutic window 150 can have its drawbacks, as explained in FIG. 8. In most stimulation circuitry designs, the amplitude is set by a digital amplitude bus <A>, which may comprise part of the signals issued on bus 118 (FIG. 5) to the stimulation circuitry 28. This digital amplitude bus <A> typically comprises a number of bits, and in the example of FIG. 8 eight bits A8:A1 are assumed. This allows 256 different amplitude values A to be set, ranging from A=0 (<A>='00000000') to A=255 (<A>='11111111'). Digital amplitude bus <A> may carry its eight bits in parallel or in series.

The stimulation circuitry 28 outputs a current, Iout, which is proportional to the amplitude value A set by bus <A>. In one example, A=255 may yield a maximum output current amplitude Iout=25.5 mA, which is the maximum current the stimulation circuitry can produce. This means each time the amplitude value A is incremented, Iout increases by 0.1 mA. In other words, and as shown in the graph of FIG. 8, the amplitude values A can range from 0, 1, 2, 3, . . . , 254, 255, which produces Iout with a value of 0, 0.1, 0.2, 0.3, . . . , 25.4, 25.5 mA. Iout can in turn be provided by the stimulation circuitry 28 to an electrode node 39, which can in turn pass the current to a corresponding electrode 16 as explained earlier. Note that the digital amplitude bus <A> may need to be sent independently to both to PDAC and NDAC circuits to produce +Iout and −Iout, but this subtlety isn't shown in FIG. 8.

While it may be useful to limit current amplitude I to a therapeutic window 150 in light of sensed neural responses, this can limit current adjustment in undesirable ways. For example, assume a therapeutic window 150 has been defined as shown in FIG. 8 in which Imin equals 4.0 mA and Imax equals 7.5 mA. This corresponds to amplitude values on the digital amplitude bus of Amin=40 and Amax=75. In other words, amplitude values A of 39 or less, or 76 or more, would be prohibited, because these would produce currents with amplitudes outside of the window 150. This means the patient can only adjust the current amplitude in 36 steps. This is wasteful of the stimulation circuitry 28's capability, which as noted earlier can handle 255 amplitude steps. Further, the resolution of these 36 steps is constant and is set to 0.1 mA per step. This resolution may be too coarse, especially when the therapeutic window 150 is narrow for a given patient. If therapeutically useful amplitudes are limited to a narrow window 150, it may be useful to increase or decrease the current amplitude in lower current increments. For example, when incrementing or decrementing the amplitude value A, it may be desirable to increment or decrement the current by less than 0.1 mA, such as by 0.05 mA, 0.01 mA, etc. However, this is not possible in traditional stimulation circuitries 28 that have a fixed resolution, i.e., a fixed current increment per amplitude value step.

This issue is addressed according to the invention by programming the stimulation circuitry 28 with a therapeutic window 150 determined in response to neural response testing. Such programming of the stimulation circuitry 28 may involve programming one or more of a minimum current amplitude (Imin) and/or a maximum current amplitude (Imax). Programming the stimulation circuitry allows an expanded range of amplitude values, and preferably all usable amplitude values supported by the stimulation circuitry, to be used to set the current within the therapeutic window. This causes the resolution to be decreased, because each increment of the amplitude value A provides a smaller increment to the current amplitude Tout produced by the stimulation circuitry.

FIGS. 9A-9D show a first example of stimulation circuitry 200 that can be programmed to be constrained to operate within a therapeutic window 150 of current amplitudes, while still allowing all values of amplitude A to be used (e.g., from 0 to 255) to navigate this window. Stimulation circuitry 200 may be used in place of stimulation circuitry 28 described earlier. Stimulation circuitry 200 is disclosed and discussed in detail in U.S. patent application Publication 2022/0321139, filed Mar. 10, 2022, which is incorporated by reference in its entirety. Because the reader is assumed familiar with the stimulation circuitry 200 disclosed in '139 Publications, it is only briefly summarized here with respect to FIGS. 9A-9D.

Figures 9A, 9B:
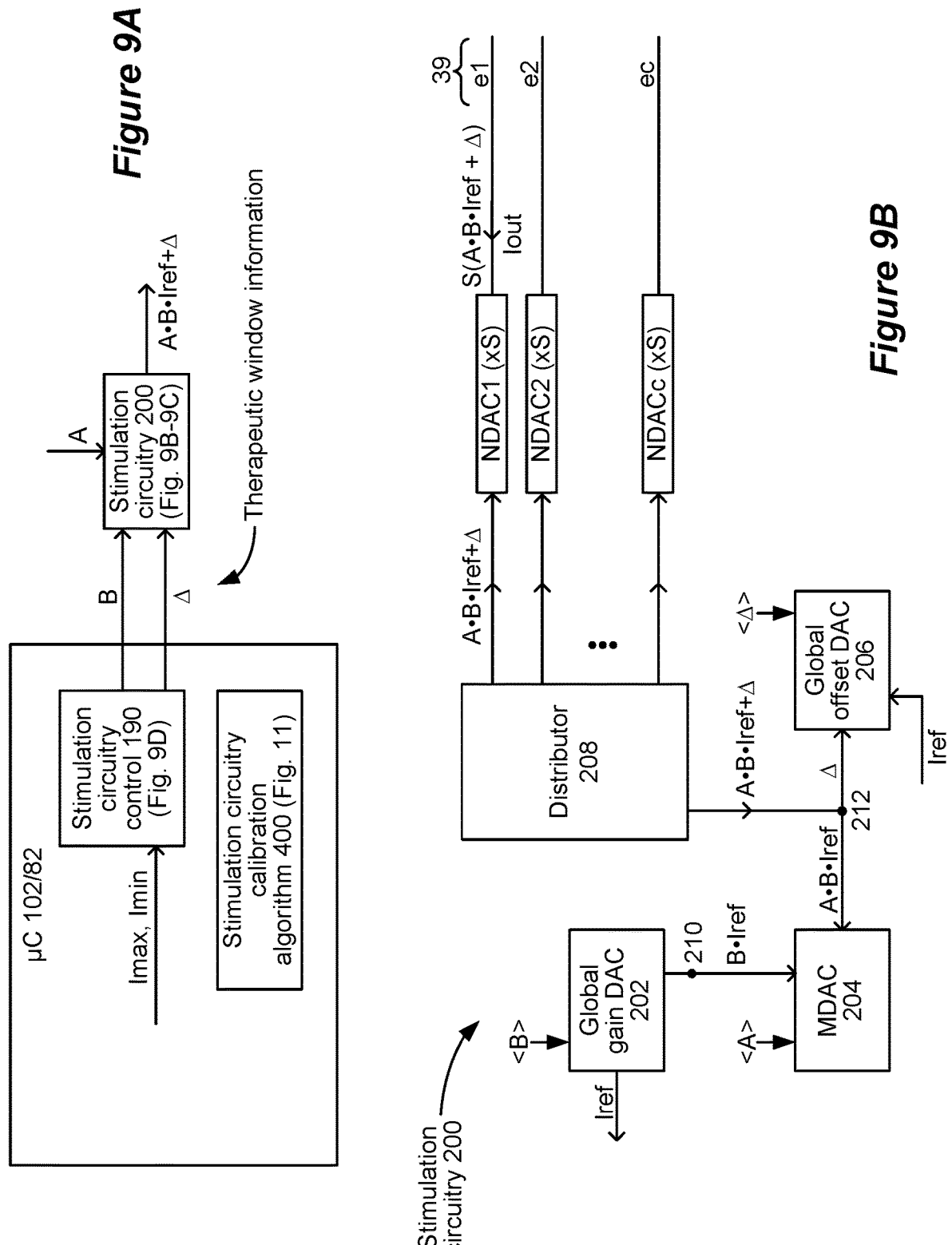

FIG. 9A shows the logic circuitry involved in programming stimulation circuitry 200 to operate in a therapeutic window 150. In this example, stimulation circuitry control logic 190 receives Imin and/or Imax as determined earlier via neural sensing algorithm 124. Logic 190 can be programmed into the control circuitry 102 of the IPG 100, or the control circuitry 82 of an external system such as those discussed earlier (FIG. 3). Logic 190 determines values B and A which are indicative of the therapeutic window 150 that will constrain operation of the stimulation circuitry 200, as explained further below. If B and A are determined in an external system, their values can be transmitted to the IPG 100. The stimulation circuitry 200 also receives an amplitude value A provided by a digital amplitude bus <A> as before to set the amplitude of the output current, Tout. As explained further below, all useable amplitude values A are valid; no amplitude values A are prohibited because all values will produce an amplitude for Tout within the therapeutic window 150. Control circuitry can also include a stimulation circuitry calibration algorithm 400, which is explained further below with reference to FIG. 11.

Figure 9C:
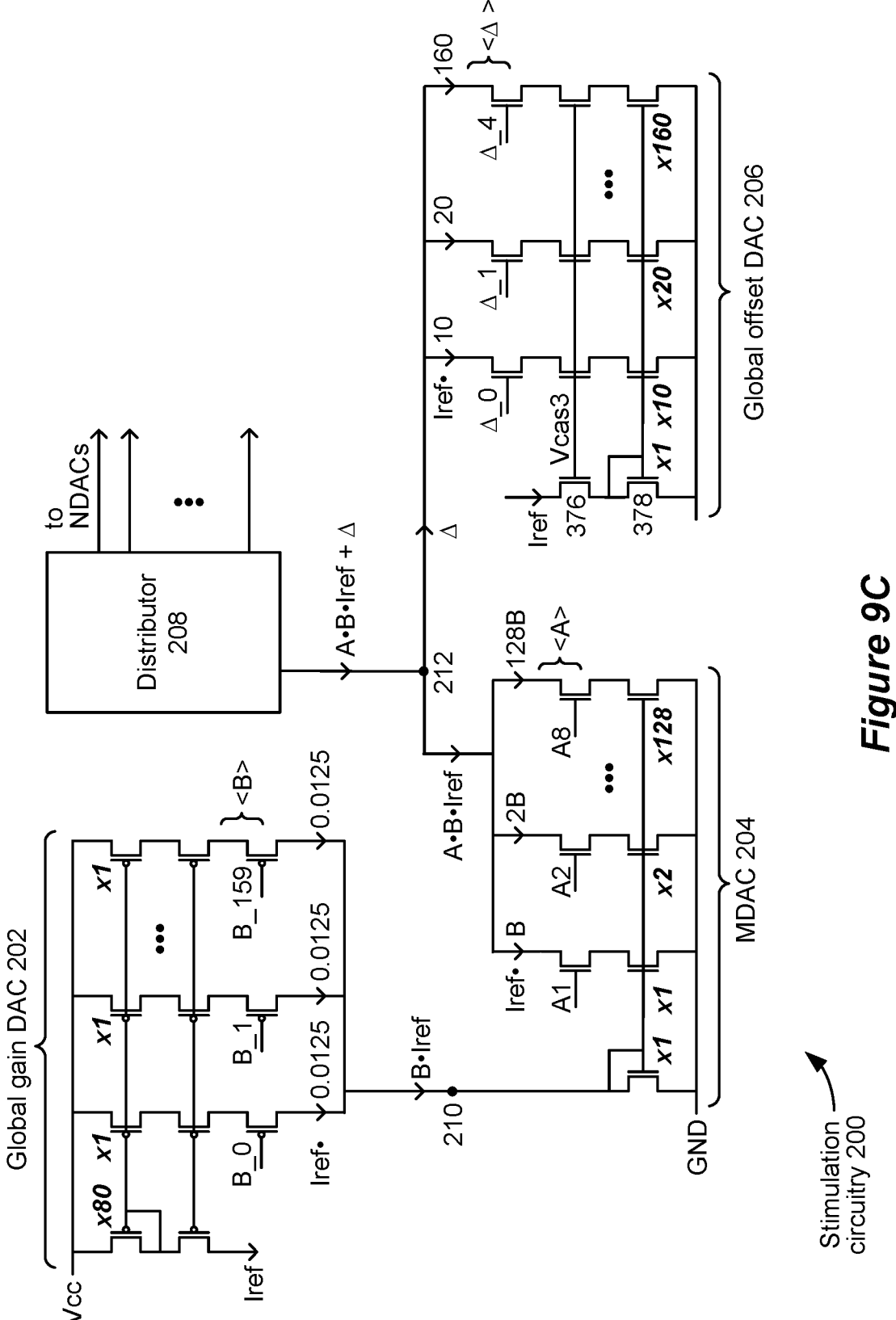

FIG. 9B shows stimulation circuitry 200 at a high level, while FIG. 9C shows further details of circuit blocks within the stimulation circuitry 200. As explained in the '139 Publication, the stimulation circuitry 200 may be duplicated to produce both anodic (sourced) and cathodic (sunk) currents from the electrodes. For simplicity, only portions of stimulation circuitry 200 used to form cathodic currents are shown, and these currents are assumed to have positive current values.

While stimulation circuitry 200 could be designed differently, the example shown in FIG. 9B starts at a global gain DAC 202, which scales a reference current (Iref) by a global gain value B, thus producing B*Iref at node 210. FIG. 9C shows further details of the global gain DAC 202, which essentially comprises current mirror circuitry that mirrors Iref to a number of different branches selected by control signals B_0 to B_159 contained within a global gain bus <B>. In this example, these control signals allow B to be set between 0.0125 and 2.0.

The current B*Iref output from the global gain DAC 202 at node 210 is input to a master DAC (MDAC) 204. This master DAC 204 receives the digital amplitude bus <A>, and uses current mirror circuitry to scale the input current B*Iref by the amplitude value A specified by digital amplitude bus <A>. Thus, the master DAC 204 produces a current A*B*Iref at node 212. As in earlier examples, amplitude values A can range from 0 to 255 as set by control signals A8 to A1.

Global offset DAC 206 uses current mirror circuitry to produce an offset current A at node 212, thereby forming a total current A*B*Iref+A at node 212. Offset current A in this example can be set by global offset bus <Δ> via control signals Δ_0 to Δ_4 contained within a global offset bus <Δ>. This sets offset current Δ from 0 to 310*Iref in increments of 10*Iref.

Current A*B*Iref+Δ at node 212 is input to a distributor 208, which copies it (perhaps with some calibration as discussed in the '139 Publication), and sends it to DACs dedicated to each of the electrode nodes. FIG. 9B assumes the use of NDACs which would provide cathodic currents at the electrodes, but again PDACs could also be dedicated at each of the electrode nodes to produce anodic currents. As best seen in FIG. 9B, each of the NDACs (and/or PDACs) can impart a scalar S to the received currents, and so can produce S(A*B*Iref+Δ) at each of the electrode nodes as Tout. Scalar S may be adjustable, but in this example it is assumed that S is set to 1000, such that the current at each electrode node (when activated by the NDAC or PDAC) is 1000(A*B*Iref+Δ).

(Notice that if the stimulation circuitry 200 is programmed with B equal to 1, and with Δ equal to zero, it essentially works as described earlier in FIG. 8, where the full range of amplitude values A allows Tout to be produced from 0 to the maximum current (e.g., 25.5 mA) that the circuitry can produce. For example, if Iref=100 nA, then Tout=1000(A*100 nA)=0.1 mA*A. Thus, when A=0, Iout=0, and when A=255 then Iout=25.5 mA. Such programming of the stimulation circuitry 200 does not constrain operation to a therapeutic window 150 of amplitudes, and could therefore be said to comprise "normal" operation of stimulation circuitry 200).

FIG. 9D explains how the stimulation circuitry control logic 190 operates to produce values for B and Δ given Imin and Imax. As shown at the left, the global offset value Δ can be set on the basis on Imin, and the status of control signals Δ_i in bus <Δ> set accordingly. For example, if Imin=4.0 mA, and assuming that the NDACs impart a gain S=1000 to Tout, then an offset current of Δ=Imin/S=4.0 μA is needed at node 212. If Iref=100 nA, the global offset DAC 206 needs to provide a gain of 40 (4μ/100 n) to produce this 40 μA current, meaning that only control signal Δ_2 is asserted. In other words, global offset bus <Δ> is set to '00100' (i.e., a decimal value of 4 on the bus <Δ>.

As shown at the right, the global gain value B can be set on the basis on Imax and Imin, and the status of control signals B_i in bus <B> set accordingly. Normal operation of the stimulation circuitry 200 (B=1, Δ=0) imparts a nominal slope of 0.1 as A is adjusted ([25.5−0]/[255−1]). By contrast, the desired slope given the therapeutic window 150 is 0.0138 ([7.5−4.0/255−1]). A global gain B=0.138 (0.0138/0.1) therefore needs to be set in the global gain DAC 202. The closest value to this that the global gain DAC 202 can produce is 0.1375 (i.e., a decimal value of 11 on the bus <B>). This can be produced by asserting only 11 of the global gain control signals B_i (e.g., B_10 to B_0) in the global gain bus <B>.

In short, stimulation circuitry 200 so programmed will produce Imin=4.0 mA when the amplitude value A is at its lowest useable value (preferably A=1 as explained in a moment), and will produce Imax=7.5 mA when amplitude A is at its highest value (255). A=0 may be reserved to set Iout=0 mA for safety to ensure a setting that produces no current, as explained in the '139 Publication. Notice that sets the desired therapeutic window 150 with a lower resolution: whereas the resolution provided by the unprogrammed stimulation circuitry of FIG. 8 provides a resolution of 0.1 mA/amplitude step, the programmed DAC circuitry 202 provides 0.0138 mA/amplitude step within the therapeutic window 150, as shown in the graph in FIG. 9D. This allows the clinician or patient to adjust the current using a larger number of amplitude steps (255 v. 36), but with each providing smaller current increments.

FIGS. 10A-10D show a second example of stimulation circuitry 300 that can be programmed to be constrained to operate within a therapeutic window 150 of current amplitudes, while still allowing all values of amplitude A to be used (e.g., from 0 to 255) to navigate this window. Stimulation circuitry 300 may be used in place of stimulation circuitry 28 described earlier. Stimulation circuitry 300 is disclosed and discussed in detail in U.S. Patent Application Publication 2021/0275798, which is incorporated by reference in its entirety. Because the reader is assumed familiar with the stimulation circuitry 300 disclosed in '798 Publication, it is only briefly summarized here with respect to FIGS. 10A-10D.

Figures 10A, 10D:
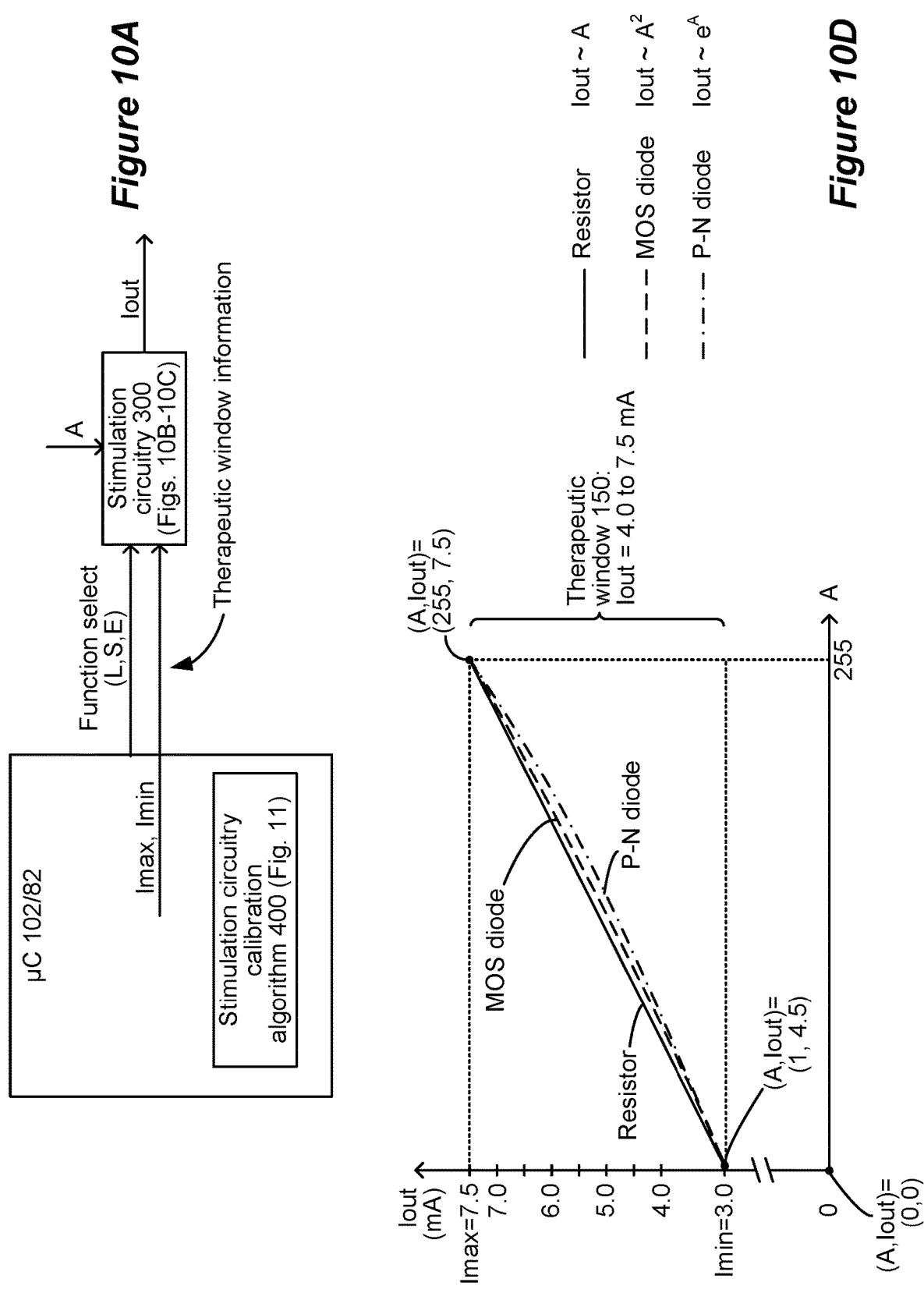
FIGS. 10A-10D show a second example of stimulation circuitry that can be programmed with therapeutic window information determined from neural response sensing. Again in this example, the digital amplitude values are not limited despite operation being constrained to the therapeutic window, which allows the adjustment of the amplitude within the therapeutic window in smaller current increments.

FIG. 10A shows the logic circuitry involved in programming stimulation circuitry 300 to operate in a therapeutic window 150. Unlike the previous example of FIGS. 9A-9D, stimulation circuitry control logic is unnecessary (compare 190, FIG. 9A), because the stimulation circuitry 300 can directly receive Imin and Imax as determined earlier via e.g., via neural sensing algorithm 124. If Imin and Imax are determined in an external system FIG. 3), their values can be transmitted to the IPG 100. The stimulation circuitry 300 also receives an amplitude value A provided by a digital amplitude bus <A> as before to set the amplitude of the output current, Iout. As in the earlier example, all amplitude values A are valid; no useable amplitude values A are prohibited because all values will produce an amplitude for Iout within the therapeutic window 150. Control circuitry can also include the stimulation circuitry calibration algorithm 400 discussed further below with reference to FIG. 11.

Figures 10B, 10C:
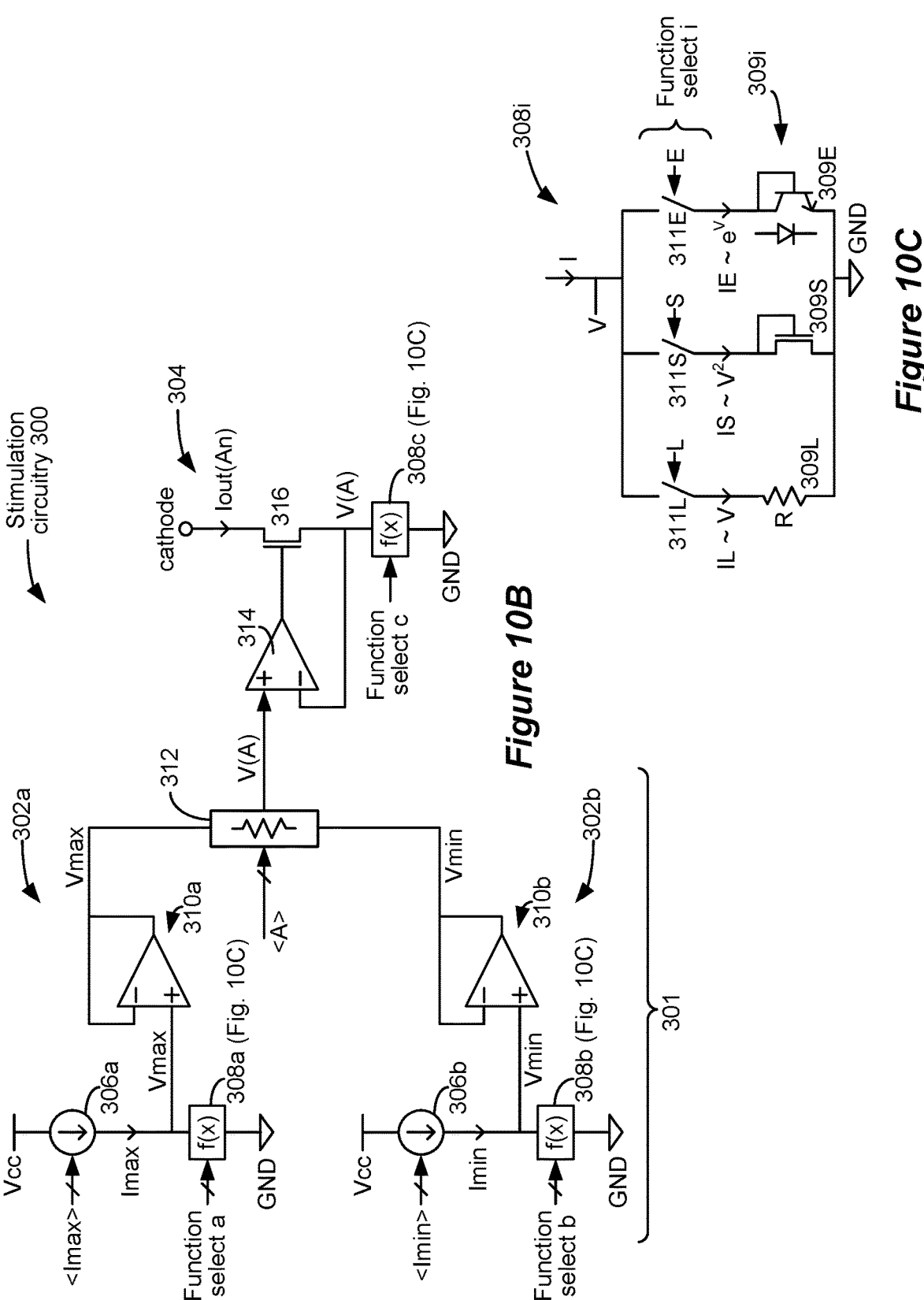

FIG. 10B shows stimulation circuitry 300 at a high level, while FIG. 10C shows further details of circuit blocks within the stimulation circuitry 300. In an actual implantation, the stimulation circuitry 300 may be duplicated to produce both anodic (sourced) and cathodic (sunk) currents from the electrodes. For simplicity, only portions of stimulation circuitry 300 used to form cathodic currents are shown, and these are assumed to have positive current values.

As shown, the stimulation circuitry 300 receives a digital amplitude bus <A> and produces an analog output current, Iout, which is a function of the amplitude, A, carried by the bus. However, as described further below, the output current Iout may not necessarily linearly scale with the amplitude A with the therapeutic window 150. That is, Iout(A) may not be incrementable in constant current increments as amplitude value A is incremented, and thus Iout may not necessarily be linearly proportional to A. The digital amplitude bus <A> as before can comprise eight bits carried in parallel or series.

The stimulation circuitry 300 as shown in FIG. 10B includes an input stage 301 and an output stage 304. The input stage 301 in this example includes two biasing stages 302a and 302b. These biasing stages 302a/b can be similar in design, and are used to set the maximum (Imax) and minimum (Imin) values for Iout to affect the desired therapeutic window 150. Biasing stage 302a includes a current source 306a which is programmable via digital bus <Imax> to produce Imax. Similarly, biasing stage 302b includes a current source 306b which is programmable via digital bus <Imin> to produce Imin. Note that the current sources 306a/b can comprise any design for a programmable current source, as discussed in the '798 Publication.

The maximum and minimum currents Imax and Imin are in this example provided to current-voltage (I-V) selection blocks 308a and 308b (generally 308i), which is shown in further detail in FIG. 10C. I-V selection blocks 308i allows different circuits 309i to be selected to receive Imax and Imin produced by the current sources 306a/b. Preferably, each of the different circuits 309i has a different current-to-voltage (I-V) response, and three different circuits 309i are shown in FIG. 10C.

A first of the circuits 309L comprises a resistor, whose current IL is linearly proportional to the voltage across it: IL~kV, where k equals the conductance of the resistor (1/R). A second of the circuits 309S comprises a MOS diode, which can be formed as shown by connecting the drain of a MOS transistor to its gate. As is known, the current flowing through this MOS diode, IS, is proportional to the square of the voltage across it: $IS~k(V-Vt)^2$, where k is a constant, and Vt comprises the threshold voltage of the MOS transistor. A third of the circuits 309E comprises a p-n diode, which can be formed in one example by connecting the collector of a bipolar junction transistor to its base. As is known, the current flowing through this p-n diode, IE, is exponentially proportional to voltage V across it: $IE~m*e^{n*V}$, where m and n are constants.

Any of these circuits 309L, 309S, and 309E can be selected for use within the I-V selection blocks 108i by closing switches 311L, 311S, 311E in series with each. These switches are respectively controlled by control signals L (linear), S (square), and E (exponential), which together comprise function select signals. These function select signals are issued by the relevant control circuitry (102, 82) as shown in FIG. 10A. Function select signals may be issued in groups a, b, and c to independently control the selection of the circuit 3109i in I-V selection block 308a, I-V selection block 308b, and a third I-V selection block 308c appearing in the output stage 304 which will be discussed later. Alternatively, the control circuitry would select the same circuit 309i in each of the I-V selection blocks 308a, 308b, and 308c, and thus send the same function control signals to all blocks 308i.

In biasing stage 302a, Imax is provided to the selected circuit 309i within I-V selection block 308a, which in turn produces a voltage Vmax as governed by the I-V characteristics of the selected circuit. For example, if resistor 109L is selected, Vmax will equal Imax*R. If MOS diode 309S is selected, Vmax would be proportional to SQRT(Imax). If p-n diode 309E is selected, Vmax would be proportional to the ln(Imax). Vmax is provided to a voltage follower 310a to produce a buffered version of Vmax at its output. Biasing stage 302b is similar, with Imin provided to the selected circuit 309i within I-V selection block 308b, which in turn produces a voltage Vmin as governed by the I-V characteristics of the selected circuit. Vmin is provided to a voltage follower 310b to produce a buffered version of Vmin at its output.

Vmax and Vmin as buffered are provided to a resistance block 312 in the input stage 301, which is controlled by the digital amplitude bus <A> to produce a voltage V(A) that varies with the amplitude value A carried by the bus. An example of resistance block 312 as provided in the '798 Publication includes a demultiplexer to process the amplitude bus signals <A>, and to use the resulting demultiplexed signals to control a resistor ladder. Again, these details are in the '798 Publication. Ultimately, the amplitude A causes the resistance block 312 to output a voltage V(A) between and including Vmax and Vmin. Thus, when A=1, V(A)=Vmin. When A=255, V(A)=Vmax. V(A) scales linearly between Vmin and Vmax for other values of A. As described earlier, it may be desirable for safety to reserve an amplitude (A=0) that specifies that the stimulation circuitry 300 should provide no output, i.e., that Tout should equal zero (as opposed to Imin).

V(A) is provided to the output stage 304 of the stimulation circuitry 300. Specifically, V(A) is provided to a non-inverting input of an operational amplifier (op amp) 314, whose output is provided to the gate of an output transistor 316. The inverting input of the op amp 314 is connected to the top of I-V selection block 308c. Feedback will force the output transistor 316 on to an extent necessary to cause the voltages at the op amp's inputs to be the same; hence V(A) will be dropped across I-V selection block 308c. This voltage drop V(A) induces a current Tout through the I-V selection block 308c and the output transistor 316 in accordance with the I-V characteristics of the circuit 309i (FIG. 5B) selected in block 308c.

Operation of the stimulation circuitry 300, and the relevance of selecting different of the circuits 309i, is explained with reference to FIG. 10D. As in the earlier example, it is assumed that stimulation circuitry 300 is programmed with Imin=4.0 mA and Imax=7.5 mA. FIG. 10D shows the response of the stimulation circuitry 300 assuming that the same circuits 309i are selected in each of the I-V selection blocks 308a-c.

Each of the selectable circuits 309i in the I-V selection blocks 308i provides a different scaling to the current Tout as amplitude value A is changed. In other words, the selected circuit 309i changes the shape of Iout(A) between Imin and Imax, as explained in further detail in the '798 Publication. For example, selection of resistors 309L provides a linear response to Tout as a function of amplitude A. The selection of MOS diodes 309S provides a squared or parabolic response to Tout as a function of amplitude A. The selection of p-n diodes 309E provides an exponential response to Tout as a function of amplitude A.

The '798 Publication explains that selecting these different circuits 309i can have different advantages. For example, selecting a linear response (resistors 309L) keeps the current increment constant as the amplitude values A are incremented. In effect, the resolution provided in this implementation is the same as discussed earlier for stimulation circuitry 200 (FIGS. 9A-9D). Selecting a squared or parabolic response (MOS diodes 309S) causes the current increment to scale with amplitude value A, such that lower current increments result at lower values for A, and higher current increments result at higher values for A. Selecting an exponential response (p-n diodes 309E) causes the current increment to increase exponentially as the amplitude value is incremented. This is interesting, because each increment of the amplitude value will cause the current to be incremented by a constant percentage. Again, further details and benefits to these different selections are disclosed in the '798 Publication. In any event, stimulation circuitry 300 provides another example of circuitry that can be programmed with therapeutic window information gleaned from the neural response measurements discussed earlier.

Figure 11:
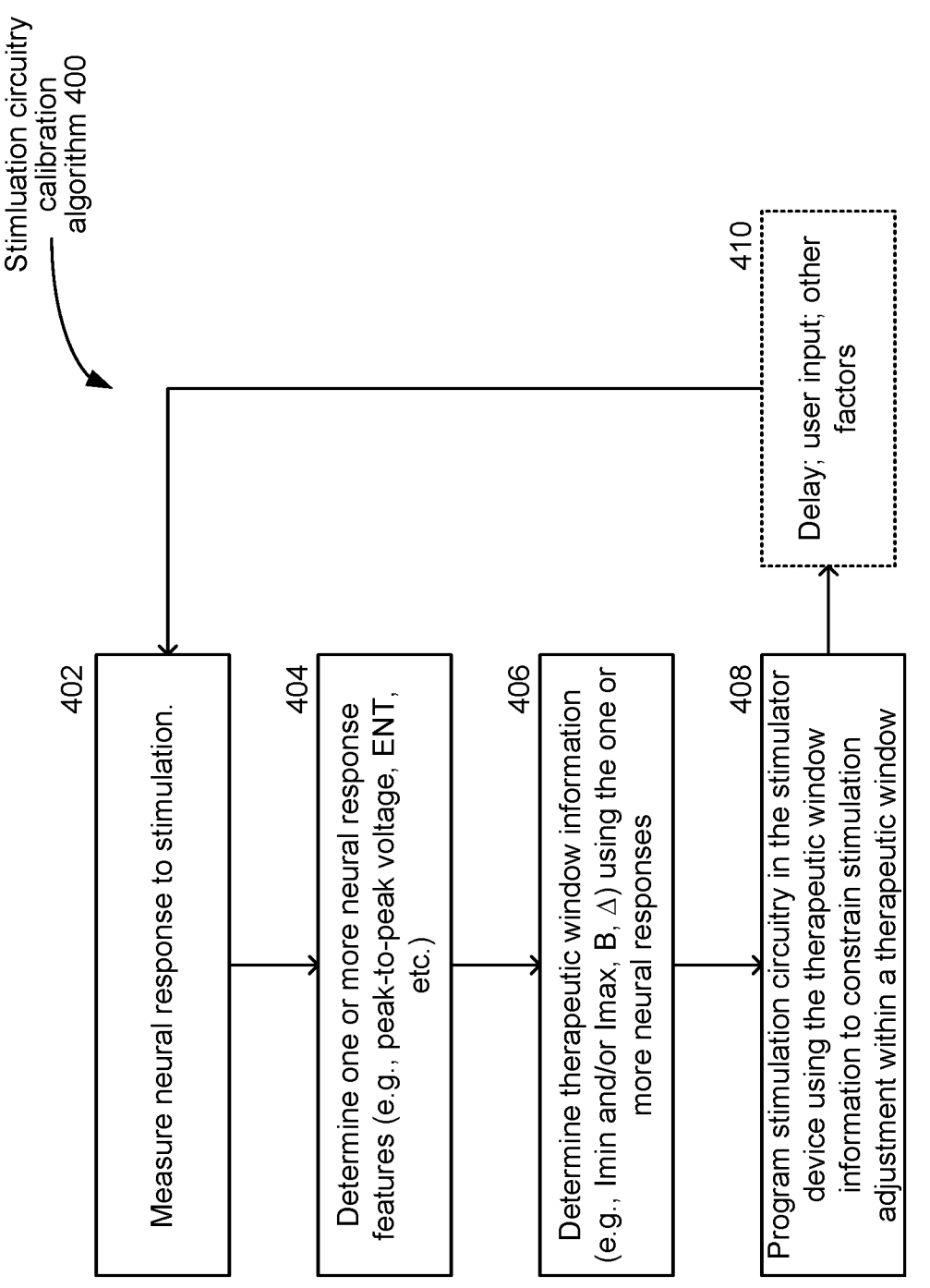
FIG. 11 shows a stimulation circuitry calibration algorithm that implements the described technique.

Operation of the disclosed techniques for calibrating stimulation circuitry to provide a therapeutic window based on neural response measurement can occur under control of a stimulation circuitry calibration algorithm 400, as shown in FIG. 11. As shown earlier in FIGS. 9A and 10A, the algorithm 400 can operate within relevant control circuitry, such as the control circuitry 102 within the IPG 100, and/or control circuitry 82 in an external system (FIG. 3). To the extent that external systems are involved in use of algorithm 400, the IPG 100 and external system can communicate information back and forth as necessary. Algorithm 400 is preferably run as a calibration procedure, and hence regular therapeutic stimulation to the patient may be interrupted while the algorithm 400 runs.

Steps 402-408 comprise main steps in the algorithm 400. At step 402, neural response to stimulation is measured, and in step 404 one or more neural response features are determined from the measured neural responses. As discussed earlier (see FIGS. 7A & 7B), relevant features can include features indicative of the size and shape of the neural responses (e.g., a peak-to-peak voltage), ENTs, and the like. As discussed earlier, the amplitude of the stimulation may be varied during these steps 402 and 404.

In step 406, information indicative of a therapeutic window 150 for a stimulation parameter (e.g., amplitude) to which the stimulation circuitry will be constrained is determined using the one or more neural features. Such information will necessarily depend on the particulars of the stimulation circuitry in the IPG 100 being programmed. Such information may include Imax and/or Imin (FIGS. 10A-10D), or other parameters indicative of Imax and/or Imin, such as B and/or Δ (FIGS. 9A-9D). In step 408, the stimulation circuitry in the IPG 100 is programmed using the therapeutic window information, thereby constraining operation of the stimulation circuitry to only allow adjustment of the stimulation parameter within the therapeutic window. Note here that constraining operation to a therapeutic window comprises constraining the stimulation parameter to a range of values (e.g., 4.0≤I≤7.5 mA) smaller than the stimulation circuitry is otherwise capable of producing (e.g., 0≤I≤25.5 mA).

Steps 402-408 calibrate the stimulation circuitry at a single point in time. However, it is also preferable that stimulation circuitry be recalibrated to affect different therapeutic windows from time to time. This is reasonable in an SCS system due to the changing nature of the implantation environment. Leads can move from their initially implanted positions in the spinal column, either because the patient moves, or simply because the leads have migrated within the spinal column over time. Scar tissue formation or physical or chemical changes to the electrodes over time may also affect ECAP sensing and/or the effectiveness of stimulation. If the leads are brought closer to the spinal column for example, larger ECAPs would generally result, and detection of those responses is made easier because of the closer proximity. This might require redetermining therapeutic window information such as Imin and Imax. For example, if larger ECAPs are sensed over time, Imax and Imin as determined earlier may be too high, and should be adjusted to lower values to generally decrease the stimulation to bring the resulting ECAPs back towards their effective baseline (as determined by Fmin and Fmax for example). Similarly, if smaller ECAPs are sensed, Imax and Imin may be too low, and should be adjusted to higher values to generally increase the stimulation to bring the resulting ECAPs towards their baseline.

To address such potential changes, optional step 410 allows the stimulation circuitry to be periodically recalibrated. ("Periodically" here doesn't necessary require recalibration at a constant time interval, but instead should be construed to mean that recalibration occurs from time to time as necessary). Step 410 can be implemented in a number of different ways. In one example, step 410 can impart a delay time before calibration (steps 402-408) is repeated. This example is particularly useful if the algorithm 400 operates wholly within the IPG 100, as it allows a new therapeutic window 150 to be established without the assistance of an external system.

Alternatively, at least portion of the algorithm 400 can operate in the control circuities 82 of external systems in communication with the IPG 100. For example, algorithm 400 can be periodically instigated by a user input at step 410, such as by selecting an option (not shown) on the GUI 90 (FIG. 4) of an external system. When such an option is selected, the external system can instruct the IPG 100 to take the necessary neural response measurements 402; other steps 404-408 can be performed by the IPG 100 and/or the external system, as discussed previously. Note that algorithm 400 can use the neural sensing algorithm 124 discussed earlier to assist in measuring neural responses and determine their features (see FIG. 5).

Still other factors can cause the algorithm 400 to repeat at step 410. For example, the IPG 100 may measure or receive other information suggesting that the current therapeutic window 150 is no longer optimal for the patient and therefore that the stimulation circuitry should be recalibrated to establish a new therapeutic window for the patient.

Various aspects of the disclosed techniques, and specifically the various algorithms and/or firmware disclosed (e.g., 124, 190, 400), whether implementable in the IPG or an external system, can be stored as instructions in a non-transitory computer-readable media associated with such system, such as in a magnetic, optical, or solid state memory. Such computer-readable media may also comprise a device readable by the IPG or an external system, such as a memory stick or a removable disk, which may reside distant from the IPG system. For example, a computer-readable media may be associated with or contained within a server or any other computer device which the IPG system can access via a network such as the Internet for example, as described earlier with reference to FIG. 3.

Although particular embodiments of the present invention have been shown and described, the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A method for calibrating stimulation circuitry using at least one first input to the stimulation circuitry, wherein the stimulation circuitry is in a stimulator device comprising a plurality of electrodes configured to contact a tissue of a patient, the method comprising:

using a second input of the stimulation circuitry to control an amplitude of stimulation at a selected one or more of the plurality of electrodes;

using control circuitry of the stimulator device to measure a neural response to the stimulation;

determining information indicative of a window of amplitudes from the measured neural response; and programming the stimulation circuitry at the at least one first input with the information to calibrate the amplitude of the stimulation at the selected one or more of the plurality of electrodes to within the window of amplitudes.

2. The method of claim 1, wherein determining the information indicative of the window of amplitudes from the measured neural response comprises:

determining one or more neural response features for the measured neural response; and determining the information indicative of the window of amplitudes from the one or more neural response features.

3. The method of claim 2, wherein the one or more neural response features comprises a feature indicative of the size or shape of the measured neural response.

4. The method of claim 2, wherein the one or more neural response features comprises a neural response amplitude.

5. The method of claim 2, wherein the one or more neural response features comprises an Extracted Neural Threshold (ENT), wherein the ENT comprises a lowest amplitude of the stimulation provided at the selected one or more of the plurality of electrodes at which a neural response is detected.

6. The method of claim 1, wherein the information indicative of the window of amplitudes comprises a minimum amplitude and a maximum amplitude of the stimulation.

7. The method of claim 1, wherein the information indicative of the window of amplitudes comprises information from which a minimum amplitude and a maximum amplitude of the stimulation is ascertained.

8. The method of claim 1, wherein the second input comprises an amplitude bus configured to carry a plurality of amplitude values to control the amplitude of the stimulation.

9. The method of claim 8, wherein the window of amplitudes comprises a minimum amplitude and a maximum amplitude, and wherein all of the plurality of amplitude values are used to set the stimulation at the selected one or more of the plurality of electrodes to within the window of amplitudes.

10. The method of claim 1, wherein the stimulation circuitry is capable of producing a range of amplitudes of the stimulation, and wherein the window of amplitudes is within and smaller than the range of amplitudes.

11. The method of claim 1, comprising measuring the neural response at one or more of the electrodes different from the selected one or more of the plurality of electrodes that provide the stimulation.

12. The method of claim 1, wherein the stimulator device comprises a spinal cord stimulator.

13. The method of claim 1, wherein the neural response comprises an Evoked Compound Action Potential (ECAP).

14. The method of claim 1, comprising performing the method is periodically.

15. The method of claim 1, comprising performing the method is periodically within the stimulator device.

16. A system, comprising:

a stimulator device comprising:

a plurality of electrodes configured to contact a tissue of a patient;

stimulation circuitry comprising at least one first input and a second input, wherein the stimulation circuitry is configured via the second input to control an amplitude of stimulation provided at a selected one or more of the plurality of electrodes;

control circuitry configured to:

measure a neural response to the stimulation, determine information indicative of a window of amplitudes from the measured neural response, and program the stimulation circuitry at the at least one first input with the information to calibrate the amplitude of the stimulation at the selected one or more of the plurality of electrodes to within the window of amplitudes.

17. The system of claim 16, wherein the information indicative of the window of amplitudes comprises a minimum amplitude and a maximum amplitude of the stimulation, or wherein the information indicative of the window of amplitudes comprises information from which a minimum amplitude and a maximum amplitude of the stimulation is ascertained.

18. The system of claim 16, wherein the stimulation circuitry is capable of producing a range of amplitudes of the stimulation, and wherein the window of amplitudes is within and smaller than the range of amplitudes.

19. A system, comprising:

a stimulator device comprising:

a plurality of electrodes configured to contact a tissue of a patient;

stimulation circuitry comprising at least one first input and a second input, wherein the stimulation circuitry is configured to control an amplitude of stimulation provided at a selected one or more of the plurality of electrodes;

control circuitry configured to:

measure a neural response to the stimulation, an external system in communication with the stimulator device, wherein the external system is configured to receive the neural response from the stimulator device, determine information indicative of a window of amplitudes from the received measured neural response, and transmit the information indicative of the window of amplitudes to the stimulator device, wherein the control circuitry is configured to program the stimulation circuitry at the at least one first input with the information to calibrate the amplitude of the stimulation at the selected one or more of the plurality of electrodes to within the window of amplitudes.

* * * * *